(12) United States Patent
Rivet et al.

(10) Patent No.: US 8,784,334 B2
(45) Date of Patent: Jul. 22, 2014

(54) SYSTEMS AND METHODS FOR OBTAINING ANALYTES FROM A BODY

(75) Inventors: Dennis J. Rivet, Chesapeake, VA (US); Roderick A. Hyde, Redmond, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 79 days.

(21) Appl. No.: 12/928,160

(22) Filed: Dec. 3, 2010

(65) Prior Publication Data
US 2011/0137204 A1    Jun. 9, 2011

Related U.S. Application Data

(63) Continuation of application No. 12/080,092, filed on Mar. 31, 2008, now Pat. No. 8,192,371, and a continuation of application No. 12/080,260, filed on Apr. 1, 2008, now Pat. No. 7,867,174.

(51) Int. Cl.
*A61B 5/00* (2006.01)

(52) U.S. Cl.
USPC .......................................................... 600/573

(58) Field of Classification Search
USPC .......................................................... 600/573
See application file for complete search history.

(56) References Cited

U.S. PATENT DOCUMENTS

| | | | |
|---|---|---|---|
| 4,159,018 A | 6/1979 | Brastad | |
| 6,043,080 A | 3/2000 | Lipshutz et al. | |
| 6,054,277 A | 4/2000 | Furcht et al. | |
| 7,163,515 B2 | 1/2007 | McNenny | |
| 7,217,356 B2 | 5/2007 | Cork et al. | |
| 7,347,843 B2 | 3/2008 | Adams et al. | |
| 2002/0169394 A1 | 11/2002 | Eppstein et al. | |
| 2002/0173732 A1 | 11/2002 | Hakky et al. | |
| 2004/0133126 A1* | 7/2004 | McNenny | 600/573 |
| 2004/0147871 A1* | 7/2004 | Burnett | 604/9 |
| 2005/0004539 A1* | 1/2005 | Brown et al. | 604/327 |
| 2006/0005673 A1 | 1/2006 | Long et al. | |
| 2006/0058731 A1* | 3/2006 | Burnett et al. | 604/29 |
| 2007/0122819 A1 | 5/2007 | Wu et al. | |
| 2008/0171559 A1 | 7/2008 | Frank et al. | |
| 2009/0137926 A1 | 5/2009 | Srinivasan et al. | |
| 2009/0246080 A1 | 10/2009 | Rivet et al. | |
| 2009/0247905 A1 | 10/2009 | Rivet et al. | |

OTHER PUBLICATIONS

Sopngmei Yuan, et al., MEMS-based piezoelectric array microjet, Microelectronic Engineering, 2002, pp. 767-772, Publisher: Elsevier Science B.V.

Carlos H. Mastrangelo, et al., Microfabricated Devices for Genetic Diagnostics, Proceedings of the IEEE, Aug. 1998, pp. 1769-1787, vol. 86, No. 8.

(Continued)

*Primary Examiner* — Max Hindenburg
*Assistant Examiner* — Renee Danega
(74) *Attorney, Agent, or Firm* — Suiter Swantz pc llo

(57) ABSTRACT

A method may include collecting at least one analyte from within a body, ejecting the collected at least one analyte from the body through at least one dermal layer of the body, and receiving the ejected at least one analyte outside the body. A system may include a means for collecting at least one analyte from within a body, a means for ejecting the collected at least one analyte from the body through at least one dermal layer of the body, and a means for receiving the ejected at least one analyte outside the body.

26 Claims, 26 Drawing Sheets

(56) References Cited

OTHER PUBLICATIONS

Anubhav Arora, et al., Needle-free delivery of macromolecules across the skin by nanoliter-volume pulsed microjets, Proceedings of the National Academy of Sciences of the United States of America, Mar. 6, 2007, pp. 1-8, Publisher: The National Academy of Sciences of the USA, Published in: US.

* cited by examiner

200 

```
210
collecting at least one analyte from within a body 802
    collecting at least a portion of at least one of cells, proteins,
    bacteria, blood, a blood component, molecules, viruses, viral
    particles, pathogens, parasites, malarial parasites, oglionucleotides,
    lymph, a lymph component, or cerebral spinal fluid 804
        collecting at least one of plasma or serum
```

```
220
ejecting said at least one analyte from said body through at least one
dermal layer of said body
```

```
230
receiving said at least one analyte outside said body
```

FIG. 8

SYSTEMS AND METHODS FOR OBTAINING ANALYTES FROM A BODY

RELATED APPLICATIONS

For purposes of the USPTO extra-statutory requirements, the present application constitutes a continuation of U.S. patent application Ser. No. 12/080,092, entitled SYSTEMS AND METHODS FOR OBTAINING ANALYTES FROM A BODY, naming Dennis J. Rivet and Roderick A. Hyde as inventors, filed Mar. 31, 2008, which is currently co-pending or is an application of which a currently co-pending application is entitled to the benefit of the filing date.

For purposes of the USPTO extra-statutory requirements, the present application constitutes a continuation of U.S. patent application Ser. No. 12/080,260, entitled SYSTEMS AND METHODS FOR OBTAINING ANALYTES FROM A BODY, naming Dennis J. Rivet and Roderick A. Hyde as inventors, filed Apr. 1, 2008, which is currently co-pending or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

BACKGROUND

It is often necessary or desirable to obtain analytes from a body (such as obtaining blood from a body in order to perform a glucose test and determine the glucose level of the blood). However, obtaining analytes from a body may require invasive techniques, including repeatedly puncturing the skin of the body or invasive surgery. It would be beneficial to provide a way to obtain analytes from within a body without such invasive techniques.

SUMMARY

In one aspect, a method includes but is not limited to collecting at least one analyte from within a body, ejecting the collected at least one analyte from within the body through at least one dermal layer of the body, and receiving the ejected at least one analyte outside the body. In addition to the foregoing, other method aspects are described in the claims, drawings, and text forming a part of the present disclosure.

In one or more various aspects, related systems include but are not limited to circuitry or programming for effecting the herein-referenced method aspects; the circuitry or programming can be virtually any combination of hardware, software, or firmware configured to effect the herein-referenced method aspects depending upon the design choices of the system designer.

In one aspect, system includes but is not limited to a means for collecting at least one analyte from within a body, a means for ejecting the collected at least one analyte from the body through at least one dermal layer of the body, and a means for receiving the ejected at least one analyte outside the body. In addition to the foregoing, other system aspects are described in the claims, drawings, and text forming a part of the present disclosure.

In addition to the foregoing, various other method or system or program product aspects are set forth and described in the teachings such as text (e.g., claims or detailed description) or drawings of the present disclosure.

The foregoing is a summary and thus may contain simplifications, generalizations, inclusions, or omissions of detail; consequently, those skilled in the art will appreciate that the summary is illustrative only and is NOT intended to be in any way limiting. Other aspects, features, and advantages of the devices or processes or other subject matter described herein will become apparent in the teachings set forth herein.

BRIEF DESCRIPTION OF THE FIGURES

FIG. 8 illustrates an alternative embodiment of the operational flow of FIG. 2.

DETAILED DESCRIPTION

Figure 1A:
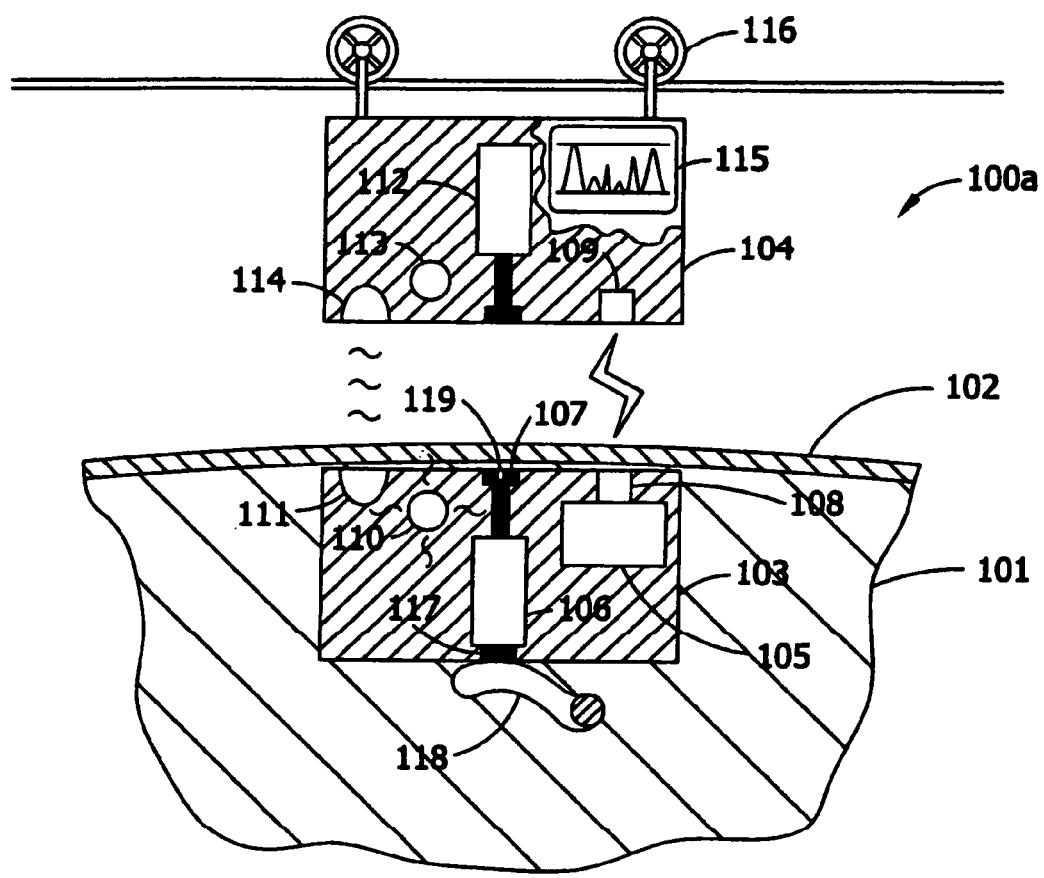
FIG. 1a is a schematic of a system for obtaining an analyte from a body.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1B:
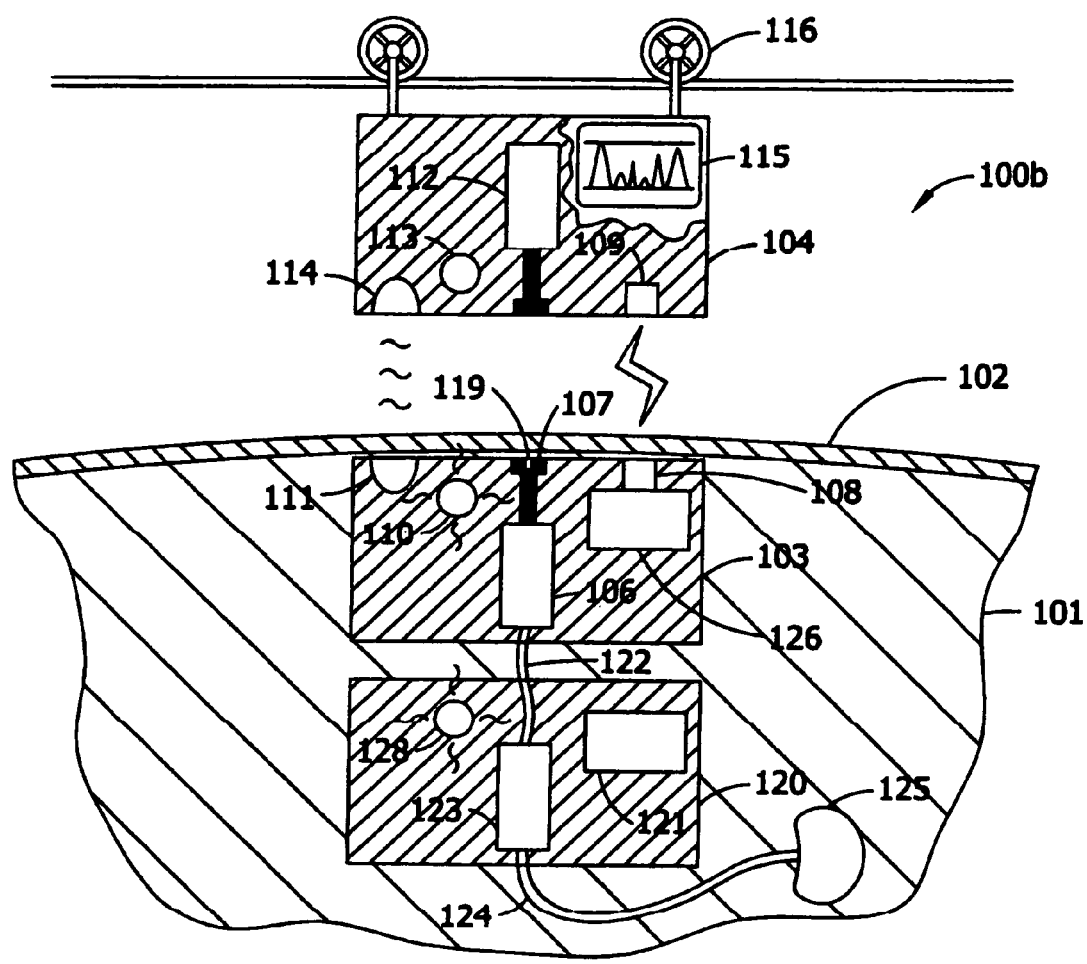
FIG. 1b is a schematic of a system for obtaining an analyte from a body.
Figure 1C:
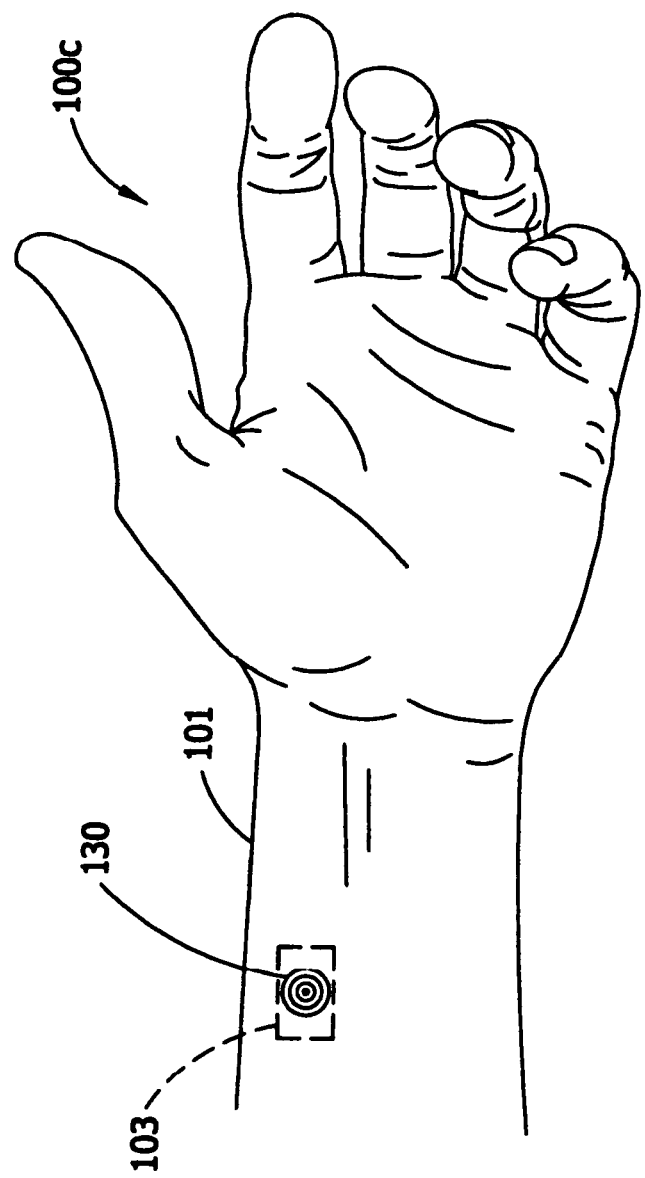
FIG. 1c is a schematic of a body including a system for obtaining an analyte from the body.

Referring generally to FIGS. 1a and 1c, a discharging device 103 and a receiving device 104 for obtaining an analyte from a body 101 are described in accordance with various embodiments. The body 101 may generally include any biological entity having a protective skin covering, such as a mammalian entity (e.g. a human, a dog, a cat, or another mammal), an avian entity (e.g. a bird of prey), as well as other biological entities having protective skin coverings. The discharging device 103 collects at least one analyte from within the body 101. Then the discharging device 103 ejects the collected at least one analyte from the body 101 through at least one dermal layer 102 of the body 101. In some embodiments, the at least one analyte may be collected and later ejected after being stored in receptacle 106. In alternative embodiments, the at least one analyte may be collected and immediately ejected without being stored in receptacle 106. Then the receiving device 104 receives the ejected at least one analyte that has been ejected from the body 101 through the at least one dermal layer 102.

The at least one analyte may be generally defined as any material within the body 101 that is obtained from the body 101. For example, the discharging device may collect at least one of blood, a blood component such as plasma or serum, cells, proteins, bacteria, cerebral fluid, cerebral spinal fluid, lymph, lymphocytes or other components of the lymphatic system, molecules, viruses, viral particles pathogens, parasites, malarial parasites, oglionucleotides, seminal fluid, semen, a therapeutic agent present in the body 101, or other materials from the body 101 or at least a portion thereof.

In some embodiments, the discharging device 103 may perform one or more operations on the at least one analyte after it has been collected. The discharging device may include a Lab-on-a-chip (LOC) (a device that integrates laboratory functions on a single chip) for performing one or more operations on the at least one analyte after it has been collected. The one or more operations may include, but are not limited to, analyzing the at least one analyte within the body, sorting the at least one analyte, concentrating the at least one analyte, and diluting the at least one analyte. For example, the discharging device 103 is illustrated with port 117 to blood vessel 118. For example, the discharging device 103 may collect blood from blood vessel 118 via port 117 and analyze the blood to determine a glucose level of the blood. By way of another example, discharging device 103 may sort the blood to isolate a blood component from the blood, such as white blood cells, blood plasma, or blood serum. Discharging device 103 may include a centrifuge mechanism configured for sorting the blood. The centrifuge mechanism may cause the blood to separate into the components of the blood based on differing densities. Denser components may separate from less dense components spatially within the centrifuge mechanism. The centrifuge mechanism may include a plurality outlets interspersed at various points such that differing blood components may exit the centrifuge mechanism via different outlets of the plurality of outlets based on their differing densities. Alternatively, discharging device 103 may include hydrophilic and hydrophobic regions. Blood may be passed through the hydrophilic and hydrophobic regions and hydrophilic portions of the blood may collect in the hydrophilic region while hydrophobic portions of the blood may collect in the hydrophobic region. Lipids, a hydrophobic portion of the blood, may be separated from the blood by collecting the portions of the blood that have collected in the hydrophobic region. Alternatively, discharging device 103 may include a surface capable of binding antibodies. The blood may be passed over the surface, binding antibodies from the blood. The blood, less the antibodies that have bound to the surface, may be removed. Then, the surface may release the antibodies, allowing the antibodies to be collected. By way of a further example, discharging device 103 may concentrate the blood by removing water from the blood, for example, by filtration. By way of yet another example, discharging device 103 may dilute the blood by adding water to the blood. It should be understood that the above examples are merely exemplary and it is contemplated that the discharging device 103 may perform other operations on blood or on one or more analytes other than blood. By way of still another example, referring to FIG. 1b, sampling device 120 is illustrated with shunt 124 to lymph node 125. Sampling device 120 may collect material from lymph node 125 via shunt 124 and may analyze the material, sort the material, concentrate the material, or dilute the material.

Referring again to FIGS. 1a through 1c, in exemplary embodiments, the discharging device 103 may eject the collected at least one analyte from the body 101 through at least one dermal layer 102 of the body 101 via ejector 107. Ejector 107 may comprise a microjet. A microjet utilizes pressure to force or displace material through an extremely small diameter opening, i.e., a micro-nozzle (for example, approximately 50-200 μm), enabling the material to penetrate at least one dermal layer of a body without substantially damaging the dermal layer. For example, ejector 107 may utilize pressure to force or displace the at least one analyte through micro-nozzle 119 enabling the at least one analyte to penetrate at least one dermal layer of a body without substantially damaging the dermal layer. In this example, micro-nozzle 119 may be approximately cylindrical in shape and have a diameter of approximately 50-150 μm. By way of another example, ejector 107 may comprise a MEMS (microelectromechanical systems) based microjet formed by a piezoelectric transducer bonded to a silicon wafer with a micro-nozzle which forces or displaces the at least one analyte through the micro-nozzle enabling the at least one analyte to penetrate at least one dermal layer of a body without substantially damaging the dermal layer. Ejector 107 may comprise a liquid microjet that utilizes pressure to force or displace a small volume of liquid through a micro-nozzle enabling the liquid to penetrate at least one dermal layer of a body without substantially damaging the dermal layer. For example, ejector 107 may utilize pressure to force or displace the at least one analyte as a liquid through micro-nozzle 119 enabling the material to penetrate at least one dermal layer of a body without substantially damaging the dermal layer. In this example, micro-nozzle 119 may be cylindrical in shape and have a diameter of approximately 50-100 µm. By way of another example, ejector 107 may comprise a MEMS-based liquid microjet formed by a piezoelectric transducer bonded to a silicon wafer with a micro-nozzle which forces or displaces the at least one analyte as a liquid through the micro-nozzle enabling the at least one analyte to penetrate at least one dermal layer of a body without substantially damaging the dermal layer. Ejector 107 may comprise a pulsed liquid microjet that utilizes pressure to force pulse of liquid through a nozzle enabling the pulse of liquid to penetrate at least one dermal layer of a body without substantially damaging the dermal layer. For example, ejector 107 may utilize pulses of pressure to force or displace liquid through micro-nozzle 119 at a frequency of approximately 1 Hz to 10 Hz enabling the material to penetrate at least one dermal layer of a body without substantially damaging the dermal layer. By way of another example, ejector 107 may comprise a MEMS-based liquid microjet formed by a piezoelectric transducer bonded to a silicon wafer with a micro-nozzle which utilizes pulses of pressure at a frequency of approximately 1 Hz to 10 Hz to force or displace the at least one analyte as a liquid through the micro-nozzle enabling the at least one analyte to penetrate at least one dermal layer of a body without substantially damaging the dermal layer.

Alternatively, ejector 107 may include a needle. The needle may be configured to be controllably deployed and retracted. The needle may be configured such that the needle does not penetrate through the at least one dermal layer 102 of the body 101 when retracted and does penetrate through the at least one dermal layer 102 of the body 101 when deployed. For example, ejector 107 may be configured to controllably deploy the needle to penetrate through the at least one dermal layer 102 of the body 101, eject the collected at least one analyte from the body 101 through the at least one dermal layer 102 of the body 101 via the needle, and then retract the needle.

In an embodiment, the discharging device 103 may eject the collected at least one analyte from the body 101 through at least one dermal layer 102 of the body 101 utilizing high pressure. High pressure may be pressure sufficient to eject at least one analyte from the body 101 through at least one dermal layer 102 of the body 101 without substantial damage to the at least one dermal layer 102 of the body 101. For example, the discharging device 103 may eject the collected at least one analyte from the body 101 through at least one dermal layer 102 of the body 101 at a velocity of at least approximately 100 m/s. Ejector 107 may include a pressure generating mechanism for generating pressure including, but not limited to, a spring-loaded pressure generating mechanism or a piezoelectric pressure generating mechanism. For example, ejector 107 may comprise an electrically powered piezoelectric actuator which displaces a plunger in an acrylic micro-nozzle to eject the at least one analyte from the body 101 through at least one dermal layer 102 of the body 101. In this example, the volume and velocity of the ejected at least one analyte may be controlled by controlling the voltage and rise time of the electrically powered piezoelectric actuator. By way of another example, ejector 107 may comprise a loaded spring which displaces a plunger in a micro-nozzle to eject the at least one analyte from the body 101 through at least one dermal layer 102 of the body 101. By way of still another example, ejector 107 may comprise a MEMS-based microjet formed by a piezoelectric transducer bonded to a silicon wafer with a micro-nozzle approximately 5-10 µm in diameter where a continuous pressure wave generated by the piezoelectric transducer propagates the at least one analyte toward the micro-nozzle to eject the at least one analyte from the body 101 through at least one dermal layer 102 of the body 101.

In an embodiment, the at least one dermal layer 102 of the body 101 may be subjected to an energy field to aid in the ejection of at least one analyte from the body 101 through the at least one dermal layer 102. Subjecting the at least one dermal layer 102 of the body 101 to the energy field may create one or more pores in the at least one dermal layer 102 or may increase the permeability of the at least one dermal layer 102, aiding in the ejection of at least one analyte from the body 101 through the at least one dermal layer 102. The energy field may include, but is not limited to, an electrical energy field or an ultrasonic energy field. The discharging device 103 or the receiving device 104 may include an energy field subjecting mechanism for subjecting the at least one dermal layer 102 to the energy field.

In an embodiment, the discharging device 103 may include a discharging transmitter 110. The discharging transmitter 110 may transmit a collected signal when the discharging device 103 has collected at least one analyte. The collected signal may include, but is not limited to, at least one of a type of the at least one analyte that has been collected, a type of the at least one analyte available to be ejected, an amount of the at least one analyte that has been collected, or an amount of the at least one analyte available to be ejected. For example, the collected signal may include that red blood cells have been collected. By way of another example, the collected signal may include that 10 µL of plasma is available to be ejected. The discharging transmitter 110 may transmit a location signal enabling the discharging device 103 to be located. The discharging transmitter 110 may transmit a finished signal when the discharging device 103 has finished ejecting the collected at least one analyte from the body 101 through at least one dermal layer 102 of the body 101. The discharging transmitter 110 may transmit signals via electrical current, an electrical field, a magnetic flux, an optical signal, a radio frequency identification, an ultrasound, a vibration, an electromagnetic signal, a force, a pressure, or any desired signal transmission medium.

In another embodiment, the receiving device 104 may be aligned with the discharging device 103 in preparation for ejection. The receiving device 104 may be aligned with discharging device 103 utilizing a motorized track system 116. Alternatively, receiving device 104 may be aligned with discharging device 103 manually. The receiving device 104 may include a signal receiver 113. The signal receiver 113 may receive a location signal transmitted by discharging device 103 to guide alignment of receiving device 104 with discharging device 103. Alternatively, the body 101 may include a fiducial 130 to guide alignment of receiving device 104 with discharging device 103. The fiducial 130 may be located in proximity to discharging device 103. Alternatively, the fiducial 130 may be located within discharging device 103. The fiducial 130 may comprise any location marker including, but not limited to, a fluorescent marker, a marker having an enhanced radio signature, a radio frequency identification tag, a radio opaque marker, a retro reflector, a magnetic signature, a conductivity signature, or an ultrasonic marker. The fiducial 130 may also comprise a tattoo on the at least one dermal layer 102 of the body 101. The receiving device 104 may include a locating device for locating fiducial 130. For example, the fiducial 130 may include a tattoo on the at least one dermal layer 102 of the body 101 and the locating device may include an optical detector. The receiving device 104 may utilize the optical detector to detect the tattoo to guide alignment of receiving device 104 with discharging device 103. By way of another example, the fiducial 130 may include a radio opaque marker located within discharging device 103 and the locating device may include a device for emitting electromagnetic radiation and detecting when the electromagnetic radiation does not pass through a material. The receiving device 104 may utilize the device to detect the radio opaque marker to guide alignment of receiving device 104 with discharging device 103. By way of a further example, the fiducial may include a conductive material with a conductivity signature and the locating mechanism may include a conductivity detector for detecting the conductivity signature of the conductive material. The receiving device 104 may utilize the conductivity detector to detect the conductive material to guide alignment of the receiving device 104 with the discharging device 103. The discharging device 103 may verify that the receiving device 104 is aligned with the discharging device 103 prior to ejecting the collected at least one analyte from the body 101 through the at least one dermal layer 102 of the body 101. The discharging device 103 may include a locating device for locating a fiducial located within the receiving device 104 and may verify that the receiving device 104 is aligned with the discharging device 103 prior to ejecting the collected at least one analyte from the body 101 through the at least one dermal layer 102 of the body 101 by detecting the fiducial. For example, the receiving device 104 may include a marker with an enhanced radio signature and the locating device may include a detector for detecting the marker with the enhanced radio signature. The discharging device 103 may verify that the receiving device 104 is aligned with the discharging device 103 prior to ejecting the collected at least one analyte from the body 101 through the at least one dermal layer 102 of the body 101 by utilizing the detector to detect detecting the marker with the enhanced radio signature included in the receiving device 104. By way of another example, the receiving device 104 may include a magnet and the discharging device 103 may include a detector for detecting a magnetic signature of the magnet. The discharging device 103 may verify that the receiving device is aligned with the discharging device 103 prior to ejecting the collected at least one analyte from the body through the at least one dermal layer of the body by detecting the magnetic signature of the magnet. Alternatively, the discharging device 103 may include a locating device for locating a fiducial located within the receiving device 104 and may verify that the receiving device 104 is in proximity with the discharging device 103 prior to ejecting the collected at least one analyte from the body 101 through the at least one dermal layer 102 of the body 101 by detecting the fiducial. The discharging device may eject the collected at least one analyte from the body 101 through the at least one dermal layer 102 of the body 101 when the fiducial included in the receiving device 104 is detected.

In an embodiment, the discharging device 103 may include a signal receiver 111. The signal receiver 111 may receive an ejection signal. The discharging device 103 may then eject the collected at least one analyte from the body 101 through at least one dermal layer 102 of the body 101 in response to the signal receiver 111 receiving the ejection signal. The signal receiver 111 may receive a stop signal. The discharging device 103 may stop ejecting the collected at least one analyte from the body 101 through at least one dermal layer 102 of the body 101 in response to the signal receiver 111 receiving the stop signal. The receiving device 104 may include transmitter 114. The receiving device transmitter 114 may transmit an ejection signal to the discharging device 103. The transmitter 114 may transmit the ejection signal via electrical current, an electrical field, a magnetic flux, an optical signal, a radio frequency identification, an ultrasound, a vibration, an electromagnetic signal, a force, a pressure or other signal transmission medium. For example, the transmitter 114 may transmit the ejection signal via a force and the signal receiver 111 may receive the ejection signal via the force. The force may be a kinetic force. The transmitter 114 may be configured to transmit the ejection signal by creating a kinetic force. The signal receiver 111 may be configured to receive the kinetic force created by the transmitter 114. The receiving device transmitter 114 may transmit the ejection signal in response to the receiving device 104 being moved into proximity with discharging device 103. For example, the receiving device 104 may receive a location signal transmitted by the discharging device 103. Based on the location signal, the receiving device 104 may determine that it is in sufficient proximity to receive the at least one analyte ejected by the discharging device 103 and receiving device transmitter 114 may then transmit an ejection signal. The receiving device 104 may include one or more processors or memory for determining proximity to the discharging device 103 based on the location signal. The receiving device 104 may be moved into proximity with discharging device 103 utilizing a motorized track system 116. Alternatively, receiving device 104 may be moved into proximity with discharging device 103 manually. The receiving device transmitter 114 may transmit a stop signal to the discharging device 103. The transmitter 114 may transmit the stop signal via electrical current, an electrical field, a magnetic flux, an optical signal, a radio frequency identification, an ultrasound, a vibration, an electromagnetic signal, a force, a pressure or other signal transmission medium. The receiving device transmitter 114 may transmit the stop signal when the receiving device 104 cannot receive any more of the collected at least one analyte.

In an embodiment, the discharging device 103 is powered by a power source which can be located inside the body 101 or located outside the body 101, or both located inside and outside the body. The receiving device 104 may include a power transfer mechanism, such as power provider 109. The discharging device 103 may include a power receiver mechanism, such as power receiver 108. The receiving device 104 may provide power to discharging device 103 via power provider 109 and power receiver 108. For example, power provider 109 may be connected to an AC power source and may provide power to the discharging device 103 via power receiver 108 utilizing the at least one dermal layer 102 as a conductive medium. Alternatively, the body 101 may include a power generating mechanism inside the body 101. For example, the power generating mechanism may include a piezoelectric strip surrounding a muscle (such as the heart). As the muscle expands or contracts, the piezoelectric strip flexes, generating power. The power generating mechanism may be coupled to discharging device 103 to provide power to discharging device 103. By way of another example, the power generating mechanism may include an energy storage mechanism 105 coupled to discharging device 103 to provide power to discharging device 103. For example, the energy storage mechanism 105 may include, but is not limited to, a lithium-ion battery, an alkaline battery, a lead acid battery, an absorbed glass mat battery, a thermal battery, a chloroaluminate battery, a nickel-zinc battery, a nickel cadmium battery, an aluminum battery, a lithium battery, or a nickel metal hydride battery. Alternatively, the power generating device may be located both inside and outside the body 101.

In another embodiment, the discharging device 103 may include an energy storage mechanism 105. For example, the energy storage mechanism 105 may include, but is not limited to, a lithium-ion battery, an alkaline battery, a lead acid battery, an absorbed glass mat battery, a thermal battery, a chloroaluminate battery, a nickel-zinc battery, a nickel cadmium battery, an aluminum battery, a lithium battery, or a nickel metal hydride battery. The energy storage mechanism 105 may be charged by a power source which is either inside the body 101 or outside the body 101 or both. The receiving device 104 may include a power transfer mechanism, such as power provider 109. The discharging device 103 may include a power receiver mechanism, such as power receiver 108. The receiving device 104 may charge the energy storage mechanism 105 via power provider 109 and power receiver 108. For example, the power provider 109 may be connected to a DC power source and a DC to AC power converter and may charge the energy storage mechanism 105 via the power receiver 108 utilizing mutual induction. Alternatively, the body 101 may include a power generating mechanism inside the body 101. For example, the power generating mechanism may include an electroactive polymer surrounding an artery. As blood flows through the artery, the electroactive polymer flexes, generating power. The power generating mechanism may be coupled to the energy storage mechanism 105 of the discharging device 103 to charge the energy storage mechanism 105 of the discharging device 103.

The receiving device 104 may include a receiving port 112, which may be enclosed in a housing, which may be configured for receiving the ejected at least one analyte that has been ejected from the body 101 through the at least one dermal layer 102. The receiving port 112 may be any receiving chamber-like device that has a closable opening. The closable opening may be, for example, controlled by a valve or a flap or by a membrane that can be pierced by ejection of the at least one analyte from the body 101 through at least one dermal layer 102 of the body 101. The membrane may be self-sealing, for example, to prevent leakage of the at least one analyte from the receiving chamber. The receiving port 112 may receive the ejected at least one analyte that has been ejected from the body 101 through the at least one dermal layer 102 through the closeable opening and may then close the closeable opening to prevent leakage of the at least one analyte from the receiving chamber.

In an embodiment, the receiving device 104 may analyze the received at least one analyte outside the body 101. The receiving device 104 may include an analysis device (including one or more processors, memories, or sensors) for analyzing the at least one analyte outside the body 101. The one or more processors, memories, or sensors for analyzing the at least one analyte outside the body 101 may comprise a LOC (such as the microfabricated genetic diagnostic devices discusses in Mastrangelo, Burns, and Burke, "Microfabricated Devices for Genetic Diagnostics," *Proceedings of the IEEE*, vol. 86, No. 8, August 1998, which is herein incorporated by reference). For example, the one or more processors, memories, or sensors for analyzing the at least one analyte outside the body 101 may comprise a microfluidic chip (such as the assay structure in microfluidic chip discussed in U.S. Publication No. 2007/0122819, which is herein incorporated by reference) including a channel on a surface of the chip of immobilized substances capable of reacting with the at least one analyte where an amount of the at least one analyte is detected by determining the length of the portion of the channel where the at least one analyte reacted with the immobilized substances. In this example, the at least one analyte may comprise blood and the immobilized substances may be capable of reacting with cholesterol in the blood such that the amount of cholesterol in the blood may be determined by determining the length of the portion of the channel where the blood reacted with the immobilized substances. By way of another example, the one or more processors, memories, or sensors for analyzing the at least one analyte outside the body 101 may comprise a MEMS based processing system (such as the biological suspension processing system discussed in U.S. Pat. No. 7,217,356, which is herein incorporated by reference) including a MEMS sensor for detecting a characteristic of the at least one analyte in a flow path. In this example, the at least one analyte may comprise blood and the MEMS sensor may comprise a microcytometer which detects fluorescently-labeled antibodies in the blood. By way of still another example, the one or more processors, memories, or sensors for analyzing the at least one analyte outside the body 101 may comprise a nucleic acid diagnostic device (such as the miniaturized integrated nucleic acid diagnostic device discussed in U.S. Pat. No. 6,043,080, which is herein incorporated by reference) including arrays of oligonucleotide probes on a surface of the device where nucleotides from the at least one analyte hybridizes on the array of oligonucleotide probes and a DNA (Deoxyribonucleic acid) sequence may be determine from where the nucleotides hybridize on the array of oligonucleotide probes. By way of yet another example, one or more processors, memories, or sensors for analyzing the at least one analyte outside the body 101 may comprise a genetic testing microchip (such as the integrated microchip genetic testing system discussed in U.S. Pat. No. 6,054,277, which herein is incorporated by reference) including a microcantilever molecular recognition surface which specific DNA from the at least one analyte bind to where the specific DNA may be detected by detecting a mass loading effect of the microcantilever molecular recognition surface. The receiving device 104 may include a display device, such as display 115, for displaying the results of analyzing the received at least one analyte. For example, the display may include, but is not limited to, a printer, an LCD (liquid crystal display), a CRT (Cathode ray tube), or an LED (light emitting diode). Alternatively, analysis of the received at least one analyte and display of the results of analyzing the at least one analyte may be performed by a device other than receiving device 104.

In an embodiment, the at least one analyte may have a useful life. The useful life of the at least one analyte may comprise the period of time when the at least one analyte is useful for a particular purpose. For example, the at least one analyte may comprise a medication stored in discharging device 103 in order to be dispensed within the body 101. The medication may have a useful life (i.e. a time period after which the medication should not be dispensed). The discharging device 103 may determine that the medication has exceeded its useful life and eject the medication from the body 101 through at least one dermal layer 102 of the body 101. A medication such as lithium carbonate may be stored in discharging device 103 which should not be dispensed after being stored for six months. The discharging device 103 may determine that the lithium carbonate has been stored longer than six months and eject the lithium carbonate from the body. By way of another example, the at least one analyte may comprise red blood cells stored in discharging device 103 to be ejected and analyzed. For example, in some circumstances, the red blood cells may have a useful life of approximately 120 days, after which time the red blood cells may be too degraded for analysis. The discharging device 103 may determine that the red blood cells have exceeded their useful life without having been ejected and analyzed and may eject the red blood cells from the body 101 through at least one dermal layer 102 of the body 101. The discharging device 103 may include a useful life determining mechanism (which may include one or more processors or memories) for determining if the at least one analyte has exceeded its useful life. Receiving device 104 may comprise a disposal device or a cleaning device to dispose of the ejected medication or clean the ejected medication from the at least one dermal layer 102.

Referring now to FIGS. 1*b* and 1*c*, in a embodiment, the collecting of at least one analyte within the body 101 and the ejecting the collected at least one analyte from the body 101 through at least one dermal layer 102 of the body 101 may be performed by separate devices. The collecting of at least one analyte from within the body 101 may be performed by sampling device 120 and the ejecting the collected at least one analyte from the body 101 through at least one dermal layer 102 of the body 101 may be performed by ejecting device 103. Sampling device 120 may collect at least one analyte within the body 101. Sampling device 120 may be located distal to ejecting device 103 and the at least one analyte may be transferred to ejecting device 103 via transfer mechanism 122, located proximal to ejecting device 103. The ejecting device 103 may include a suction mechanism to transfer the at least one analyte from the sampling device 120 to the ejecting device 103 via transfer mechanism 122. Alternatively, the sampling device 120 may include a pump mechanism to transfer the at least one analyte from the sampling device 120 to the ejecting device 103 via transfer mechanism 122. Sampling device 120 may store the at least one analyte in receptacle 123 prior to transfer of the analyte to ejecting device 103. Ejecting device 103 may store the collected at least one analyte in a receptacle prior to ejection. Alternatively, ejecting device 103 may transfer and eject the at least one analyte immediately after it is collected by the sampling device 120. Sampling device 120 and ejecting device 103 may be powered by receiving device 104 via power provider 109 and power receiver 108. Alternatively, sampling device 120 and ejecting device 103 may be powered by a power source located within the body 101 or outside the body 101, or located both inside and outside the body 101. Sampling device 120 may include energy storage mechanism 121 and ejecting device 103 may include energy storage mechanism 126. Energy storage mechanism 121 and 126 may be charged with the receiving device 104 via power provider 109 and power receiver 108. Alternatively, energy storage mechanism 121 and 126 may be charged with the power source inside the body. Ejecting device 103 may include ejecting device transmitter 110 which may transmit a location signal to aid in location of ejecting device 103 or a finished signal. Sampling device 120 may include sampling device transmitter 128 which may transmit a collected signal when the sampling device 120 has collected at least one analyte. Ejecting device 103 may include ejecting device signal receiver 111 for receiving an ejection signal and may eject the collected at least one analyte from the body 101 through at least one dermal layer 102 of the body 101 in response to receiving the ejection signal. Ejecting device signal receiver 111 may be operable to receive a stop signal and may stop ejecting the collected at least one analyte from the body 101 through at least one dermal layer 102 of the body 101 in response to receiving the stop signal. Ejecting device 103 may include a locating mechanism for detecting a fiducial located within receiving device 104. Ejecting device 103 may eject the collected at least one analyte from the body 101 through at least one dermal layer 102 of the body 101 in response to detecting the fiducial located within receiving device 104. Ejecting device 103 may verify that the receiving device 104 is aligned with the ejecting device 103 prior to ejecting the collected at least one analyte from the body 101 through at least one dermal layer 102 of the body 101. Ejecting device 103 may verify that the receiving device 104 is aligned with the ejecting device 103 prior to ejecting the collected at least one analyte from the body 101 through at least one dermal layer 102 of the body 101 by detecting the fiducial located within receiving device 104. Ejecting device 103 or sampling device 120 may perform one or more operations on the at least one analyte prior to ejection including, but not limited to analyzing the at least one analyte, concentrating the at least one analyte, sorting the at least one analyte, determining the at least one analyte has exceeded its useful life, and diluting the at least one analyte.

Figure 2:
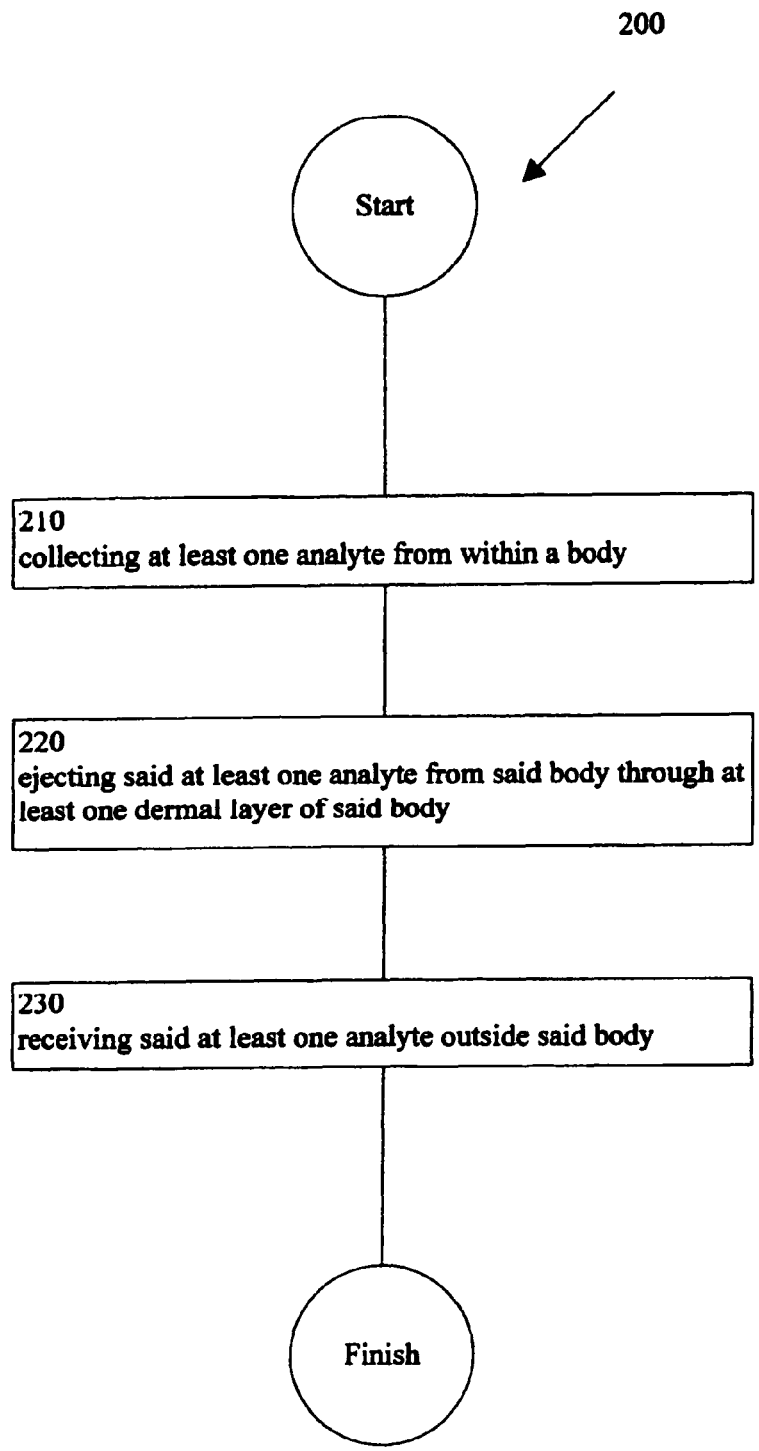
FIG. 2 illustrates an operational flow representing example operations related to obtaining an analyte from a body.

FIG. 2 illustrates an operational flow 200 representing example operations related to obtaining an analyte from a body. In FIG. 2 and in following figures that include various examples of operational flows, discussion and explanation may be provided with respect to the above-described examples of FIG. 1, or with respect to other examples and contexts. However, it should be understood that the operational flows may be executed in a number of other environments and contexts, or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to a collecting operation 210, where at least one analyte may be collected from within a body. For example, as shown in FIG. 1*b*, the sampling device 120 may collect material from lymph node 125 via shunt 124. Alternatively, the sampling device 120 may collect any material within the body 101 including, but not limited to blood or a blood component such as plasma or serum, cells, proteins, cerebral fluid, and lymphocytes or other components of the lymphatic system. The sampling device 120 may include a collection mechanism such as a port or shunt for collecting material from the body 101.

Then, in an ejecting operation 220, at least one analyte may be ejected from said body through at least one dermal layer of said body. For example, as shown in FIG. 1*b*, the ejector device 103 may eject the at least one analyte from the body 101 through at least one dermal layer 102 of the body 101. The ejector device 103 may include an ejector mechanism for ejecting the at least one analyte through at least one dermal layer 102 of the body 101 such as a pressure generating mechanism.

Then, in a receiving operation 230, at least one analyte may be received outside said body. For example, as shown in FIG. 1*b*, the receiving device 104 may receive the ejected at least one analyte. The receiving device 104 may include a receiving mechanism for receiving the ejected at least one analyte such as a test tube, or absorbency mechanism such as a sponge or rag.

Figure 3:
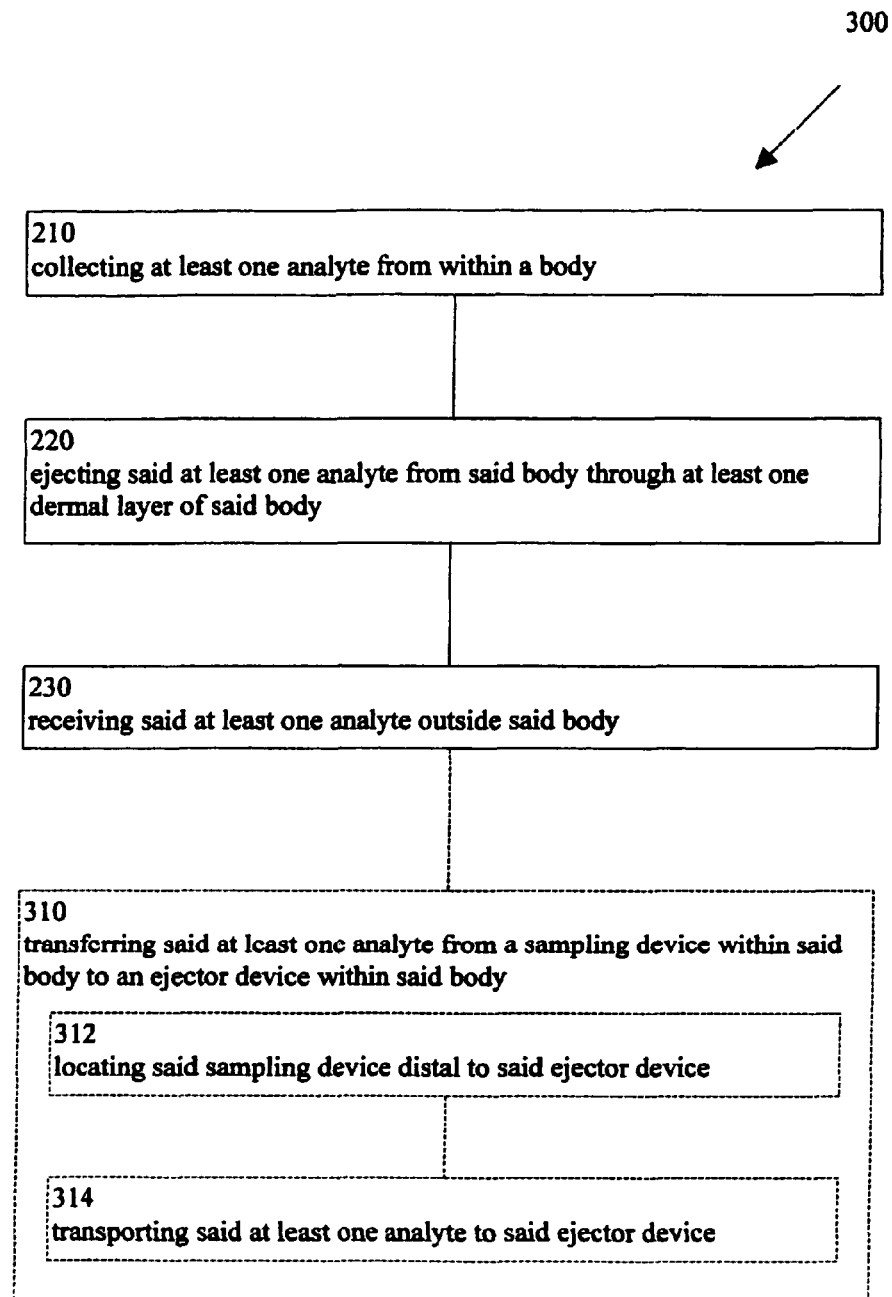
FIG. 3 illustrates an operational flow representing example operations related to obtaining an analyte from a body.

FIG. 3 illustrates an operational flow 300 representing example operations related to obtaining an analyte from a body. FIG. 3 illustrates an embodiment where the operational flow 200 of FIG. 2 may include at least one additional operation. Additional operations may include an operation 310, an operation 312, or an operation 314.

After a start operation, a collecting operation 210, an ejecting operation 220, and a receiving operation 230, the operational flow 300 moves to a transferring operation 310, where at least one analyte may be transferred from a sampling device within said body to an ejector device within said body. For example, as shown in FIG. 1*b*, the at least one analyte may be transferred from the sampling device 120 to the ejecting device 103 via the transfer mechanism 122. The transfer mechanism 122 may comprise any transfer means such as a tube or a pump system for transferring the collected analyte from the sampling device 120 to the ejecting device 103.

At the operation 312, the sampling device may be located distal to the ejector device. For example, as shown in FIG. 1, the ejecting device 103 may be located between the at least one dermal layer 102 of the body 101 and the sampling device 120. Then, at the operation 314, at least one analyte may be transported to the ejector device. For example, as shown in FIG. 1b, the ejecting device 103 or the sampling device 120 utilizes the transfer mechanism 122 to transport the collected at least one analyte from the sampling device 120 to the ejecting device 103.

Figure 4:
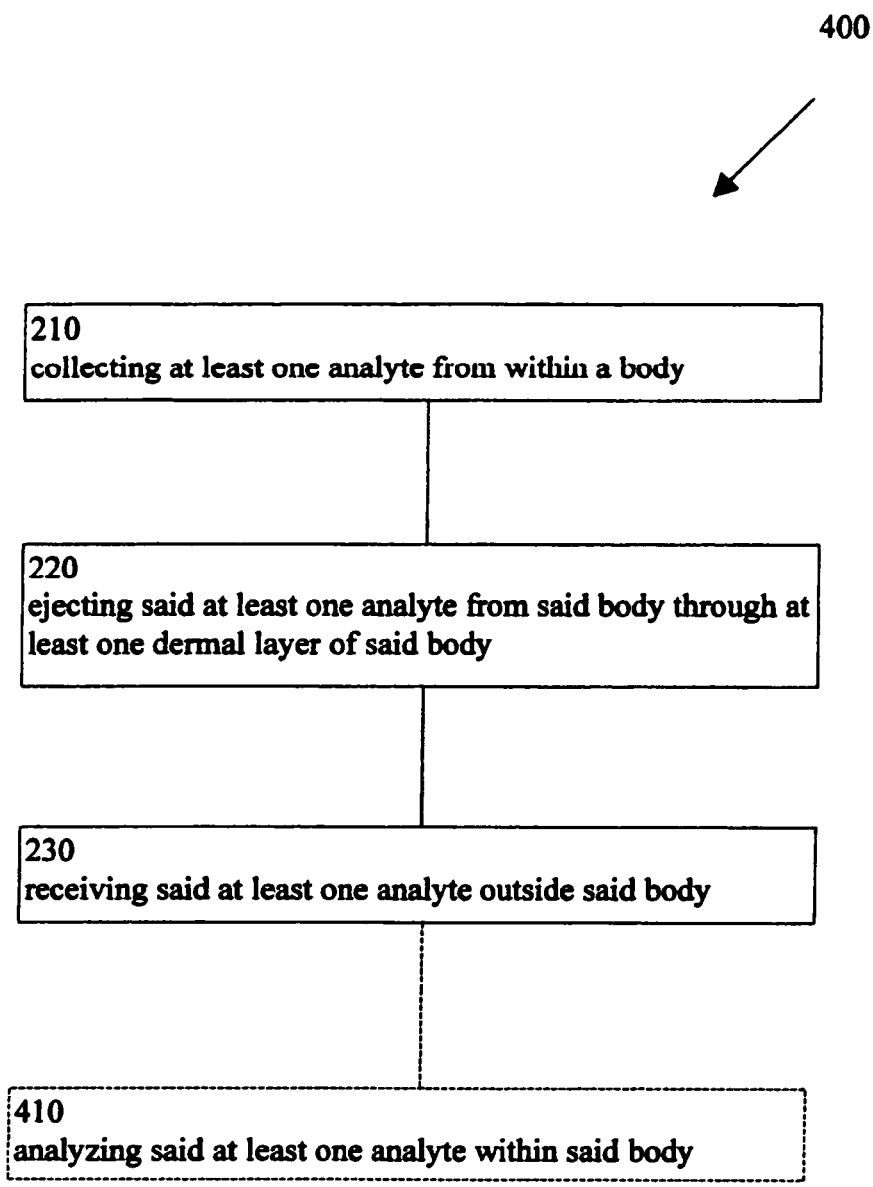
FIG. 4 illustrates an operational flow representing example operations related to obtaining an analyte from a body.

FIG. 4 illustrates an operational flow 400 representing example operations related to obtaining an analyte from a body. FIG. 4 illustrates an example embodiment where the example operational flow 200 of FIG. 2 may include at least one additional operation. Additional operations may include an operation 410.

After a start operation, a collecting operation 210, an ejecting operation 220, and a receiving operation 230, the operational flow 400 moves to an analyzing operation 410, where at least one analyte may be analyzed within said body. For example, as shown in FIG. 1b, the sampling device 120 may include a protein detector mechanism configured to detect the amount of one or more proteins in the material collected from lymph node 125 via shunt 124.

Figure 5:
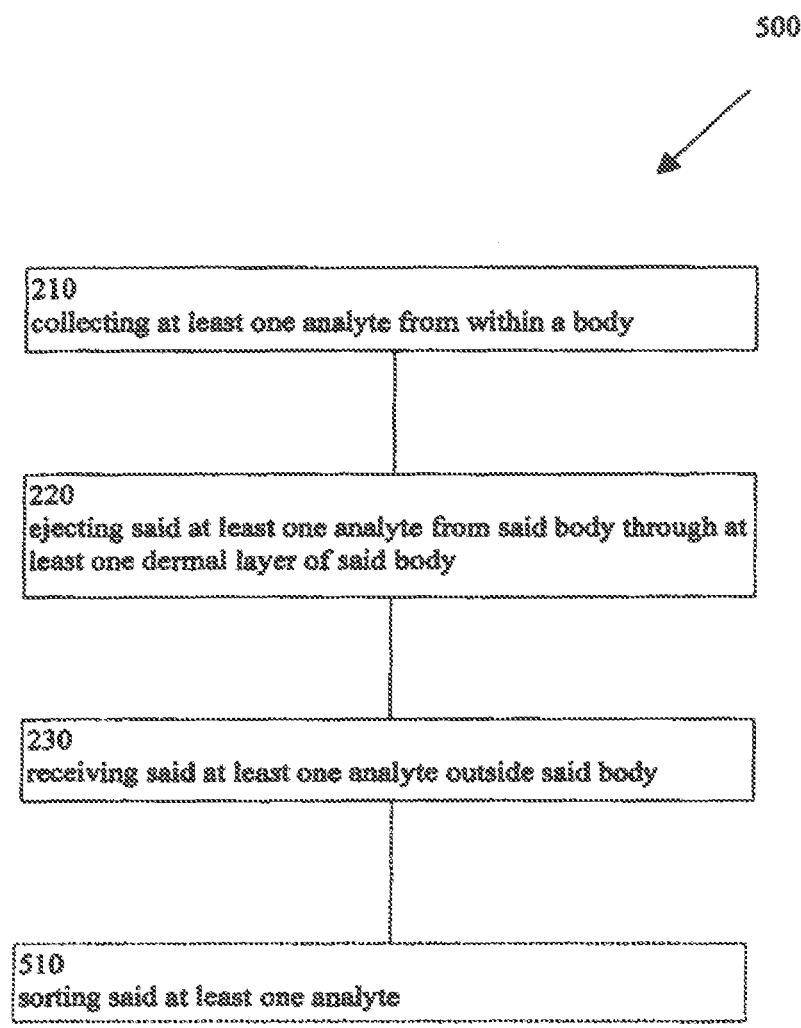
FIG. 5 illustrates an operational flow representing example operations related to obtaining an analyte from a body.

FIG. 5 illustrates an operational flow 500 representing example operations related to obtaining an analyte from a body. FIG. 5 illustrates an example embodiment where the example operational flow 200 of FIG. 2 may include at least one additional operation. Additional operations may include an operation 510.

After a start operation, a collecting operation 210, an ejecting operation 220, and a receiving operation 230, the operational flow 500 moves to a sorting operation 510, where at least one analyte may be sorted. For example, as shown in FIG. 1b, the sampling device 120 may include a sorting mechanism such as a filter or a centrifuge to sort lymphatic cells from the material collected from lymph node 125 via shunt 124.

Figure 6:
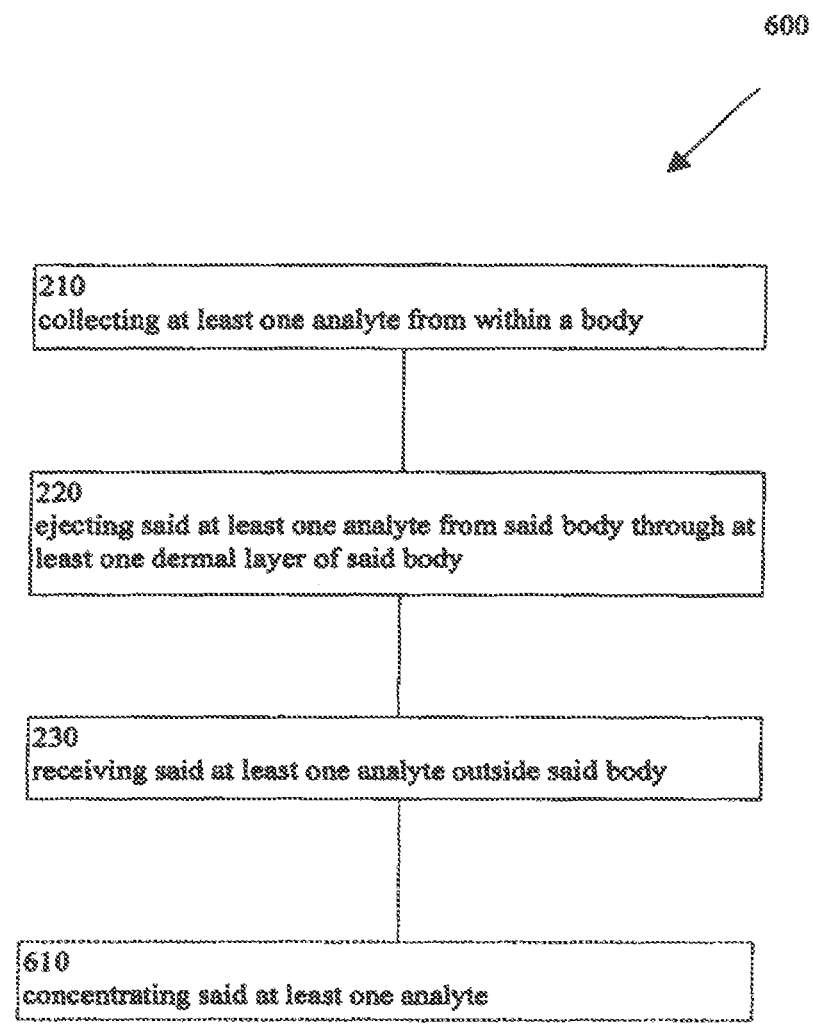
FIG. 6 illustrates an operational flow representing example operations related to obtaining an analyte from a body.

FIG. 6 illustrates an operational flow 600 representing example operations related to obtaining an analyte from a body. FIG. 6 illustrates an example embodiment where the example operational flow 200 of FIG. 2 may include at least one additional operation. Additional operations may include an operation 610.

After a start operation, a collecting operation 210, an ejecting operation 220, and a receiving operation 230, the operational flow 600 moves to a concentrating operation 610, where at least one analyte may be concentrated. For example, as shown in FIG. 1b, the sampling device 120 may include a concentrating mechanism such as a filter or centrifuge for removing water from and concentrating the material collected from lymph node 125 via shunt 124.

Figure 7:
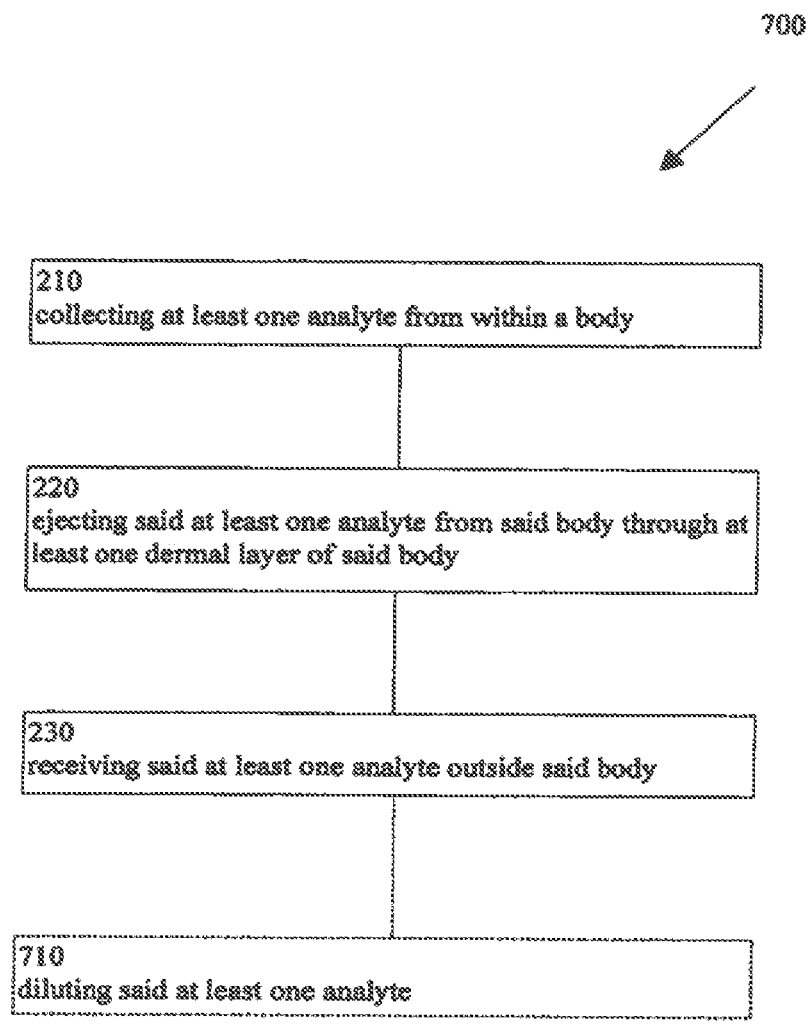
FIG. 7 illustrates an operational flow representing example operations related to obtaining an analyte from a body.

FIG. 7 illustrates an operational flow 700 representing example operations related to obtaining an analyte from a body. FIG. 7 illustrates an example embodiment where the example operational flow 200 of FIG. 2 may include at least one additional operation. Additional operations may include an operation 710.

After a start operation, a collecting operation 210, an ejecting operation 220, and a receiving operation 230, the operational flow 700 moves to a diluting operation 710, where at least one analyte may be diluted. For example, as shown in FIG. 1b, the sampling device 120 may include a water reservoir and a mixing mechanism which dilutes the material collected from lymph node 125 via shunt 124 by adding water from the reservoir to the material.

FIG. 8 illustrates alternative embodiments of the example operational flow 200 of FIG. 2. FIG. 8 illustrates example embodiments where the collecting operation 210 may include at least one additional operation. Additional operations may include an operation 802, or an operation 804.

At the operation 802, at least a portion of at least one of cells, proteins, bacteria, blood a blood component, molecules, viruses, viral particles, pathogens, parasites, malarial parasites, oglionucleotides, lymph, a lymph component, or cerebral spinal fluid may be collected. For example, as shown in FIG. 1a, the discharging device 103 may collect from blood vessel 118 via port 117 blood cells, proteins in the blood stream, bacteria in the blood stream, blood or a blood component from the blood stream. Further, at the operation 804, at least one of plasma or serum may be collected. For example, as shown in FIG. 1a, the discharging device 103 may collect plasma or serum from blood vessel 118 via port 117. The discharging device 103 may intake blood from blood vessel 118 via port 117, separate the serum or plasma from the blood, and return the separated blood back to blood vessel 118 via port 117. For example, the sampling device may separate the serum or plasma from the blood utilizing a filtration mechanism. By way of another example, the discharging device 103 may include an electrophoresis mechanism. Blood may be passed through a gel which is then charged. The components of the blood (such as proteins) may then be separated based on their electrophoretic mobility.

Figure 9:
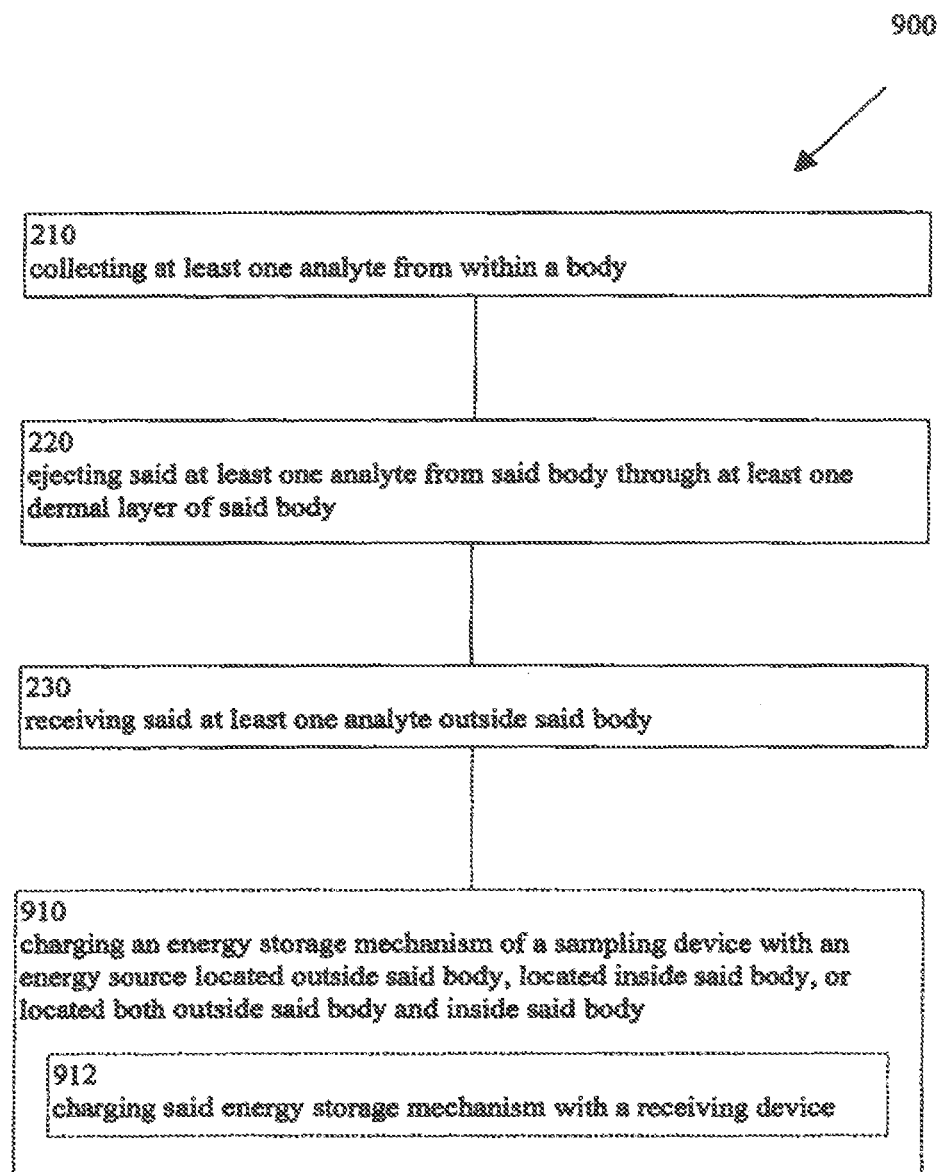
FIG. 9 illustrates an operational flow representing example operations related to obtaining an analyte from a body.

FIG. 9 illustrates an operational flow 900 representing example operations related to obtaining an analyte from a body. FIG. 9 illustrates an example embodiment where the operational flow 200 of FIG. 2 may include at least one additional operation. Additional operations may include an operation 910, or an operation 912.

After a start operation, a collecting operation 210, an ejecting operation 220, and a receiving operation 230, the operational flow 900 moves to a charging operation 910, where an energy storage mechanism of a sampling device may be charged with an energy source located outside said body, located inside said body, or located both outside said body and inside said body. For example, as shown in FIG. 1b, the energy storage mechanism 121 of sampling device 120 is charged by a power source outside said body 101 utilizing power provider 109, power receiver 108, and transfer mechanism 122. The energy storage mechanism 121 may include, but is not limited to, a lithium-ion battery, an alkaline battery, a lead acid battery, an absorbed glass mat battery, a thermal battery, a chloroaluminate battery, a nickel-zinc battery, a nickel cadmium battery, an aluminum battery, a lithium battery, or a nickel metal hydride battery. Power provider 109 may be connected to an AC power source and may charge energy storage mechanism 121 via power receiver 108 utilizing mutual induction.

At the operation 912, the energy storage mechanism may be charged with a receiving device. For example, as shown in FIG. 1b, the energy storage mechanism 121 of sampling device 120 is charged by the receiving device 104 utilizing power provider 109, power receiver 108, and transfer mechanism 122. Power provider 109 may be connected to a DC power source and may charge energy storage mechanism 121 via power receiver 108 utilizing the at least one dermal layer 102 as a conductive medium.

Figure 10:
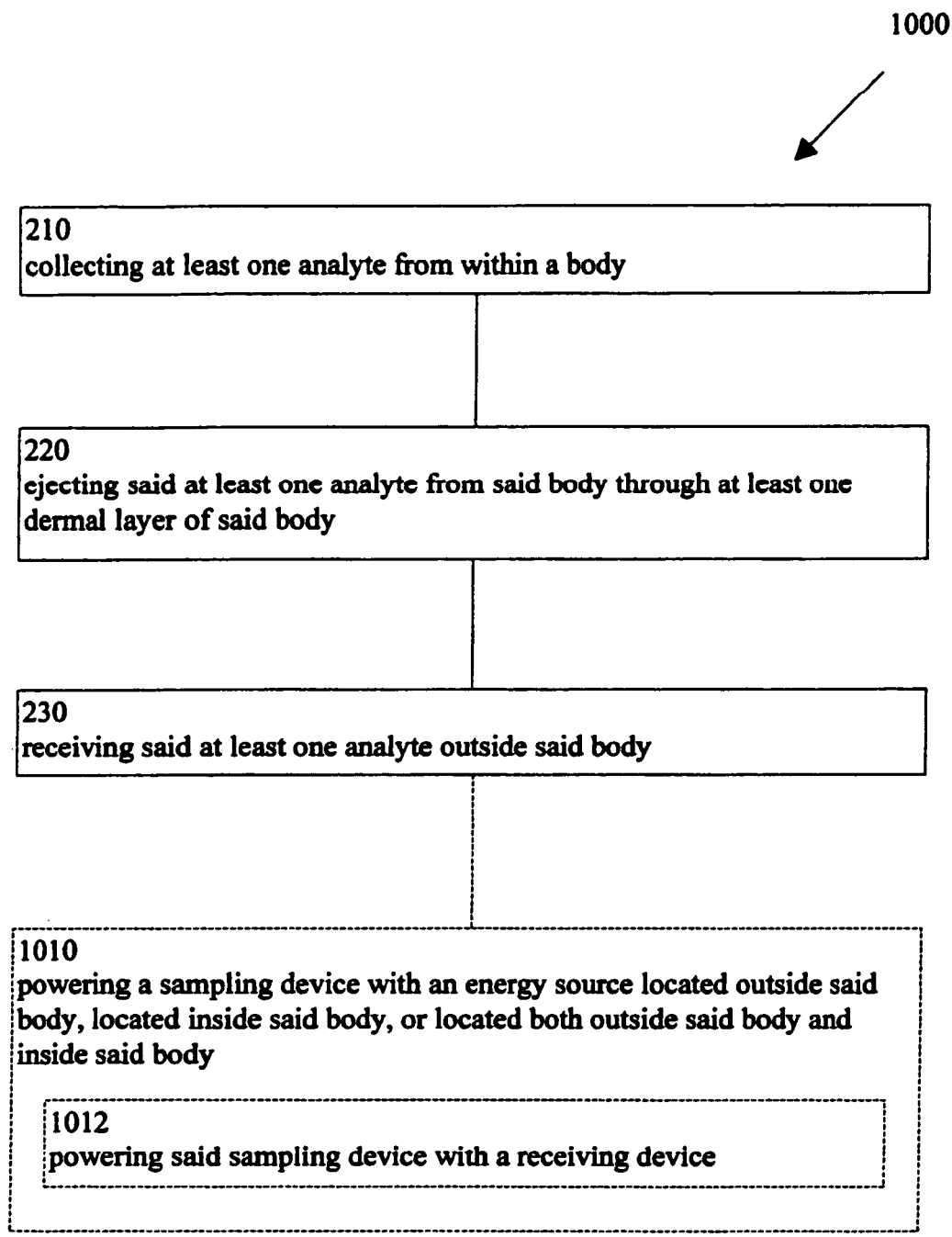
FIG. 10 illustrates an operational flow representing example operations related to obtaining an analyte from a body.

FIG. 10 illustrates an operational flow 1000 representing example operations related to obtaining an analyte from a body. FIG. 10 illustrates an example embodiment where the example operational flow 200 of FIG. 2 may include at least one additional operation. Additional operations may include an operation 1010, or an operation 1012.

After a start operation, a collecting operation 210, an ejecting operation 220, and a receiving operation 230, the operational flow 1000 moves to a powering operation 1010, where a sampling device may be powered with an energy source located outside said body, located inside said body, or located both outside said body and inside said body. For example, as shown in FIG. 1b, the sampling device 120 is powered by a power source outside the body 101 utilizing power provider 109, power receiver 108, and transfer mechanism 122. Power provider 109 may be connected to a DC power source and a DC to AC power converter and may power sampling device 120 via power receiver 108 utilizing mutual induction. By way of another example, the sampling device 120 may be powered by the energy storage mechanism 122. The energy storage mechanism 122 may include, but is not limited to, a lithium-ion battery, an alkaline battery, a lead acid battery, an absorbed glass mat battery, a thermal battery, a chloroaluminate battery, a nickel-zinc battery, a nickel cadmium battery, an aluminum battery, a lithium battery, or a nickel metal hydride battery.

At the operation 1012, the sampling device may be powered with a receiving device. For example, as shown in FIG. 1b, the sampling device 120 is powered by the receiving device 104 utilizing power provider 109, power receiver 108, and transfer mechanism 122. Power provider 109 may be connected to an AC power source and may power sampling device 120 via power receiver 108 utilizing the at least one dermal layer 102 as a conductive medium.

Figure 11:
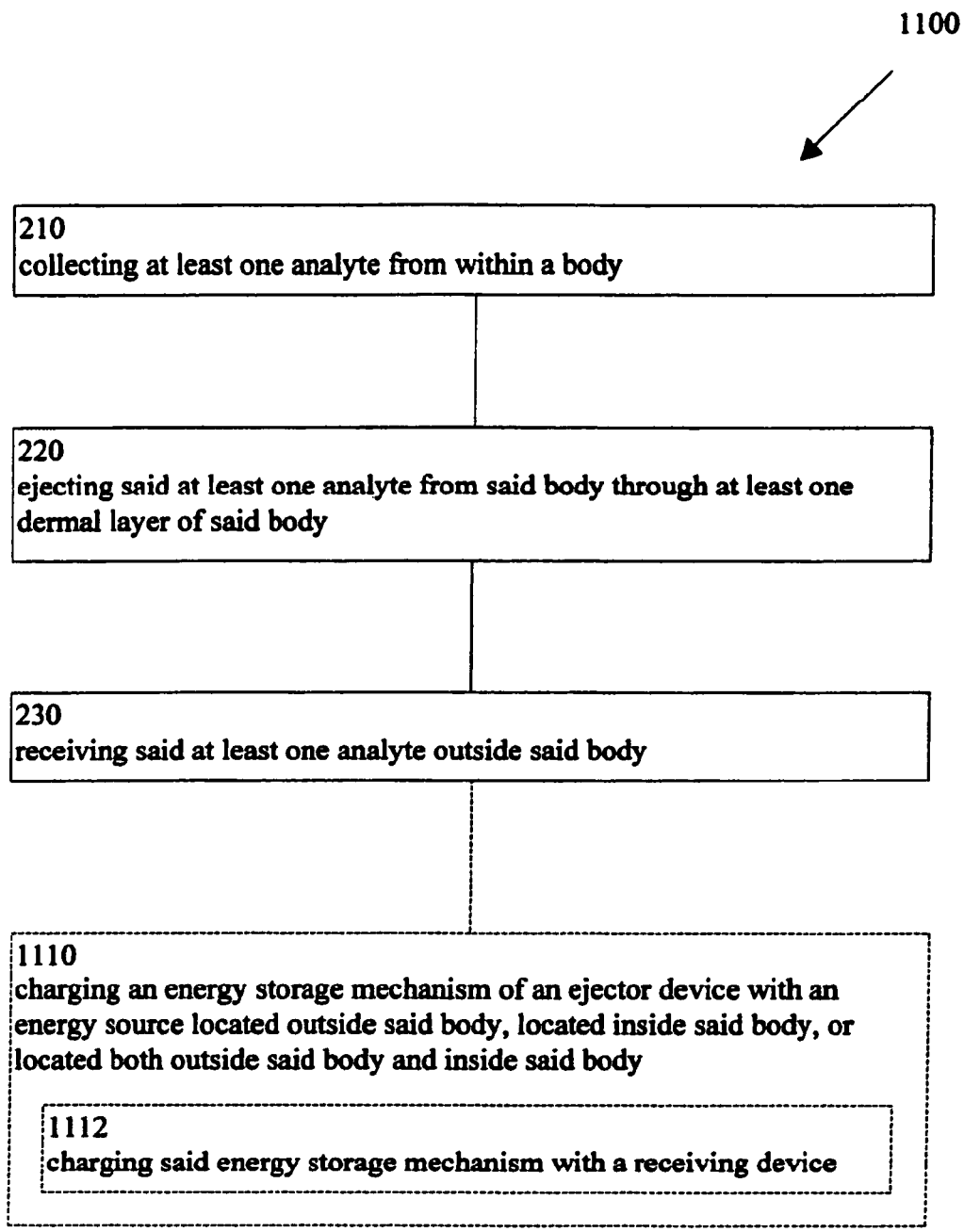
FIG. 11 illustrates an operational flow representing example operations related to obtaining an analyte from a body.

FIG. 11 illustrates an operational flow 1100 representing example operations related to obtaining an analyte from a body. FIG. 11 illustrates an example embodiment where the example operational flow 200 of FIG. 2 may include at least one additional operation. Additional operations may include an operation 1110, or an operation 1112.

After a start operation, a collecting operation 210, an ejecting operation 220, and a receiving operation 230, the operational flow 1100 moves to a charging operation 1110, where an energy storage mechanism of an ejector device may be charged with an energy source located outside said body, located inside said body, or located both outside said body and inside said body. For example, as shown in FIG. 1b, the energy storage mechanism 126 of ejecting device 103 is charged by a power source outside the body 101 utilizing power provider 109 and power receiver 108. The energy storage mechanism 126 may include, but is not limited to, a lithium-ion battery, an alkaline battery, a lead acid battery, an absorbed glass mat battery, a thermal battery, a chloroaluminate battery, a nickel-zinc battery, a nickel cadmium battery, an aluminum battery, a lithium battery, or a nickel metal hydride battery. Power provider 109 may be connected to an AC power source and may charge energy storage mechanism 126 via power receiver 108 utilizing mutual induction.

At the operation 1112, the energy storage mechanism may be charged with a receiving device. For example, as shown in FIG. 1b, the energy storage mechanism 126 of ejecting device 103 is charged by the receiving device 104 utilizing power provider 109 and power receiver 108. Power provider 109 may be connected to a DC power source and may charge energy storage mechanism 126 via power receiver 108 utilizing the at least one dermal layer as a conductive medium.

Figure 12:
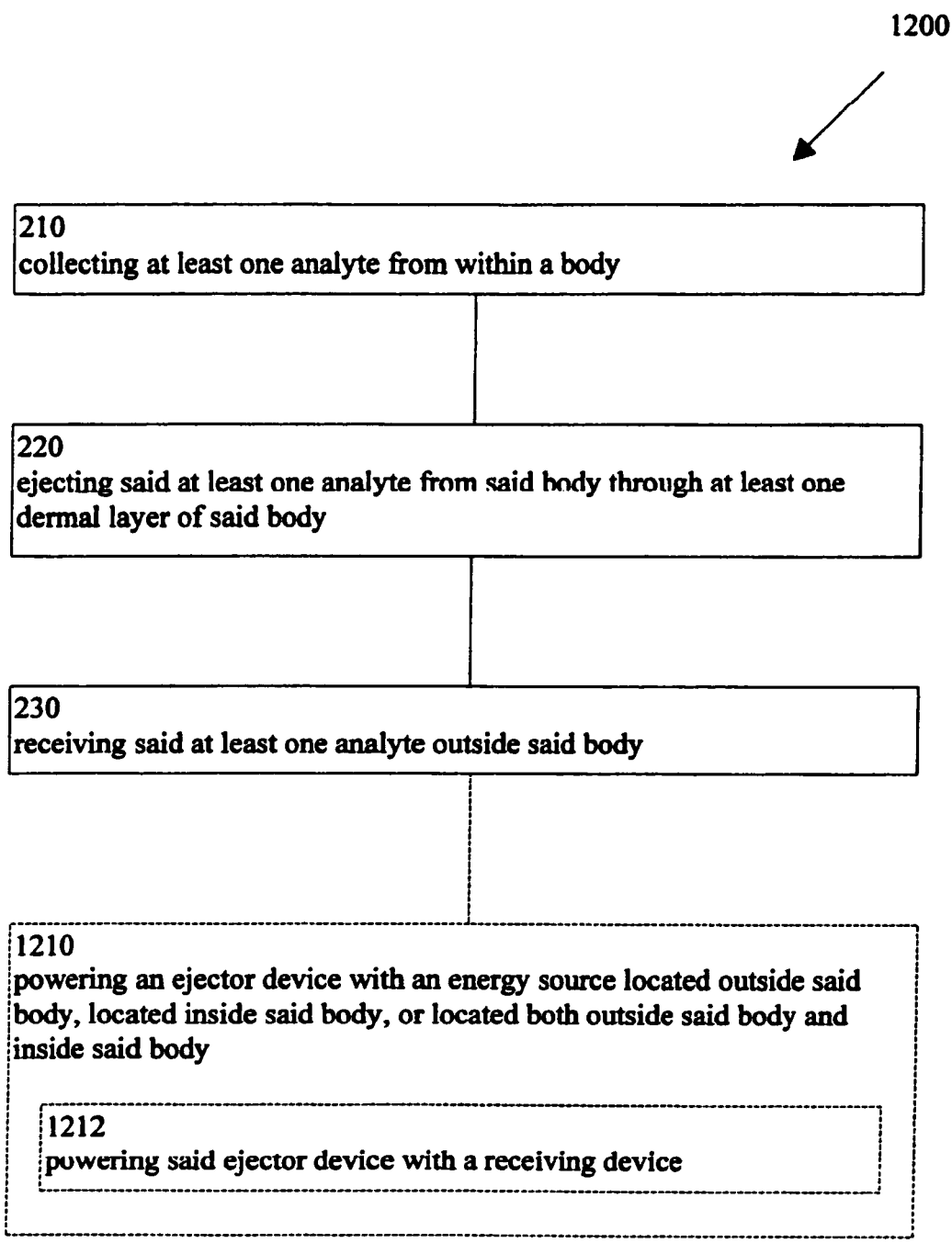
FIG. 12 illustrates an operational flow representing example operations related to obtaining an analyte from a body.

FIG. 12 illustrates an operational flow 1200 representing example operations related to obtaining an analyte from a body. FIG. 12 illustrates an example embodiment where the example operational flow 200 of FIG. 2 may include at least one additional operation. Additional operations may include an operation 1210, or an operation 1212.

After a start operation, a collecting operation 210, an ejecting operation 220, and a receiving operation 230, the operational flow 1200 moves to a powering operation 1210, where an ejector device may be powered with an energy source located outside said body, located inside said body, or located both outside said body and inside said body. For example, as shown in FIG. 1b, the ejecting device 103 is powered by a power source outside the body 101 utilizing power provider 109 and power receiver 108. Power provider 109 may be connected to a DC power source and a DC to AC power converter and may power ejecting device 103 via power receiver 108 utilizing mutual induction. By way of another example, the ejecting device 103 may be powered by the energy storage mechanism 126. The energy storage mechanism 126 may include, but is not limited to, a lithium-ion battery, an alkaline battery, a lead acid battery, an absorbed glass mat battery, a thermal battery, a chloroaluminate battery, a nickel-zinc battery, a nickel cadmium battery, an aluminum battery, a lithium battery, or a nickel metal hydride battery.

At the operation 1212, the ejector device may be powered with a receiving device. For example, as shown in FIG. 1b, the ejecting device 103 is powered by the receiving device 104 utilizing power provider 109 and power receiver 108. Power provider 109 may be connected to an AC power source and may power ejecting device 103 via power receiver 108 utilizing the at least one dermal layer as a conductive medium.

Figure 13:
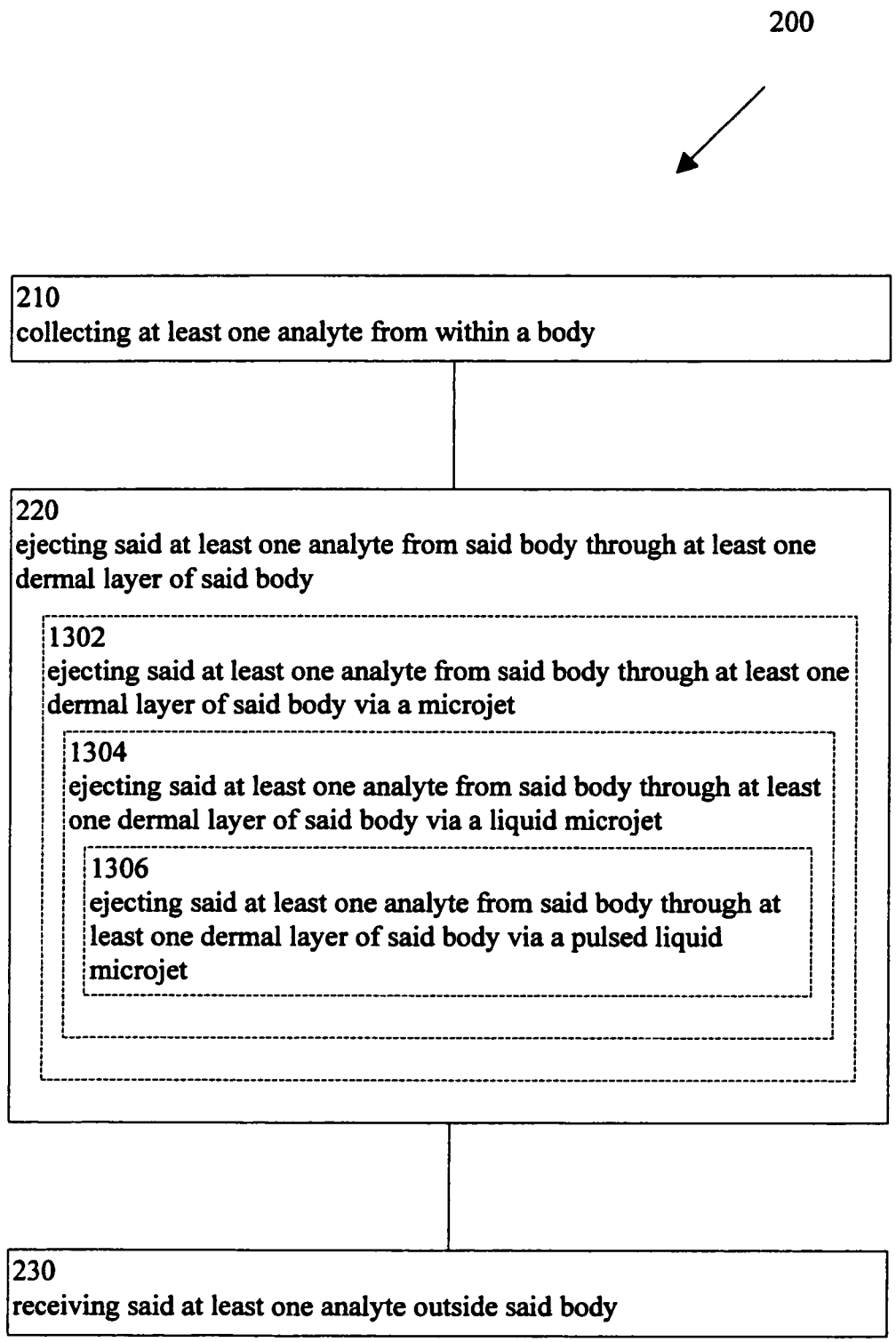
FIG. 13 illustrates an alternative embodiment of the operational flow of FIG. 2.

FIG. 13 illustrates alternative embodiments of the example operational flow 200 of FIG. 2. FIG. 13 illustrates example embodiments where the ejecting operation 220 may include at least one additional operation. Additional operations may include an operation 1302, an operation 1304, or an operation 1306.

At the operation 1302, at least one analyte may be ejected from said body through at least one dermal layer of the body via a microjet. For example, as shown in FIG. 1a, the ejecting device 103 ejects the collected at least one analyte from the body 101 through at least one dermal layer 102 of the body 101 utilizing microjet 107. Further, at the operation 1304, at least one analyte may be ejected from said body through at least one dermal layer of the body via a liquid microjet. For example, as shown in FIG. 1b, the ejecting device 103 ejects the collected at least one analyte as a liquid from the body 101 through at least one dermal layer 102 of the body 101 utilizing liquid microjet 107. Further, at the operation 1306, at least one analyte may be ejected from the body through at least one dermal layer of said body via a pulsed liquid microjet. For example, as shown in FIG. 1b, the ejecting device 103 ejects the collected at least one analyte as a liquid in a pulse from the body 101 through at least one dermal layer 102 of the body 101 utilizing pulsed liquid microjet 107. The ejecting device 103 may eject the collected at least one analyte as a liquid in a pulse in order to determine if the receiving device 104 is receiving the ejected at least one analyte prior to ejected all of the at least one analyte. The ejecting device 103 and receiving device 104 may include one or more processors, memories, transmitters, and signal receivers for determining if the receiving device 104 is receiving the ejected at least one analyte.

Figure 14:
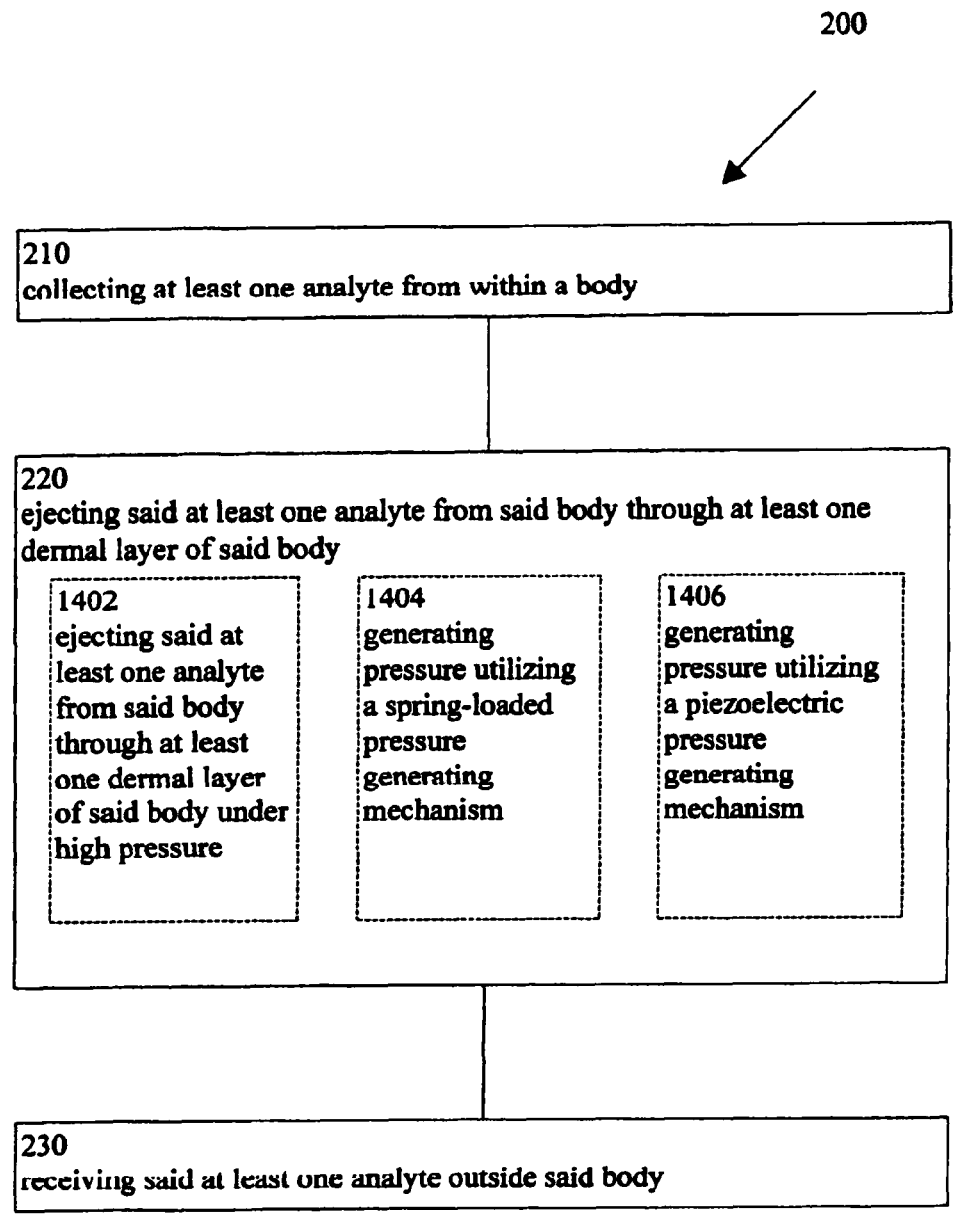
FIG. 14 illustrates an alternative embodiment of the operational flow of FIG. 2.

FIG. 14 illustrates alternative embodiments of the example operational flow 200 of FIG. 2. FIG. 14 illustrates example embodiments where the ejecting operation 220 may include at least one additional operation. Additional operations may include an operation 1402, an operation 1404, or an operation 1406.

At the operation 1402, at least one analyte may be ejected from said body through at least one dermal layer of said body under high pressure. For example, as shown in FIG. 1b, the ejecting device 103 ejects the collected at least one analyte under high pressure from the body 101 through at least one dermal layer 102 of the body 101 utilizing microjet 107. High pressure may be sufficient pressure such that the at least one dermal layer 102 of the body 101 is not substantially damaged. High pressure may allow a very thin stream to puncture an isolated portion of the at least one dermal layer 102 of the body rather than transferring the impact to a larger area of the at least one dermal layer and thus not substantially damage the at least one dermal layer 102.

At the operation 1404, a spring-loaded pressure generating mechanism may be utilized to generate pressure. For example, as shown in FIG. 1b, the ejecting device 103 ejects the collected at least one analyte from the body 101 through at least one dermal layer 102 of the body 101 via microjet 107 by generating pressure with a spring-loaded pressure generating mechanism.

At the operation 1406, a piezoelectric pressure generating mechanism may be utilized to generate pressure. For example, as shown in FIG. 1b, the ejecting device 103 ejects the collected at least one analyte from the body 101 through at least one dermal layer 102 of the body 101 via microjet 107 by generating pressure with a piezoelectric pressure generating mechanism.

Figure 15:
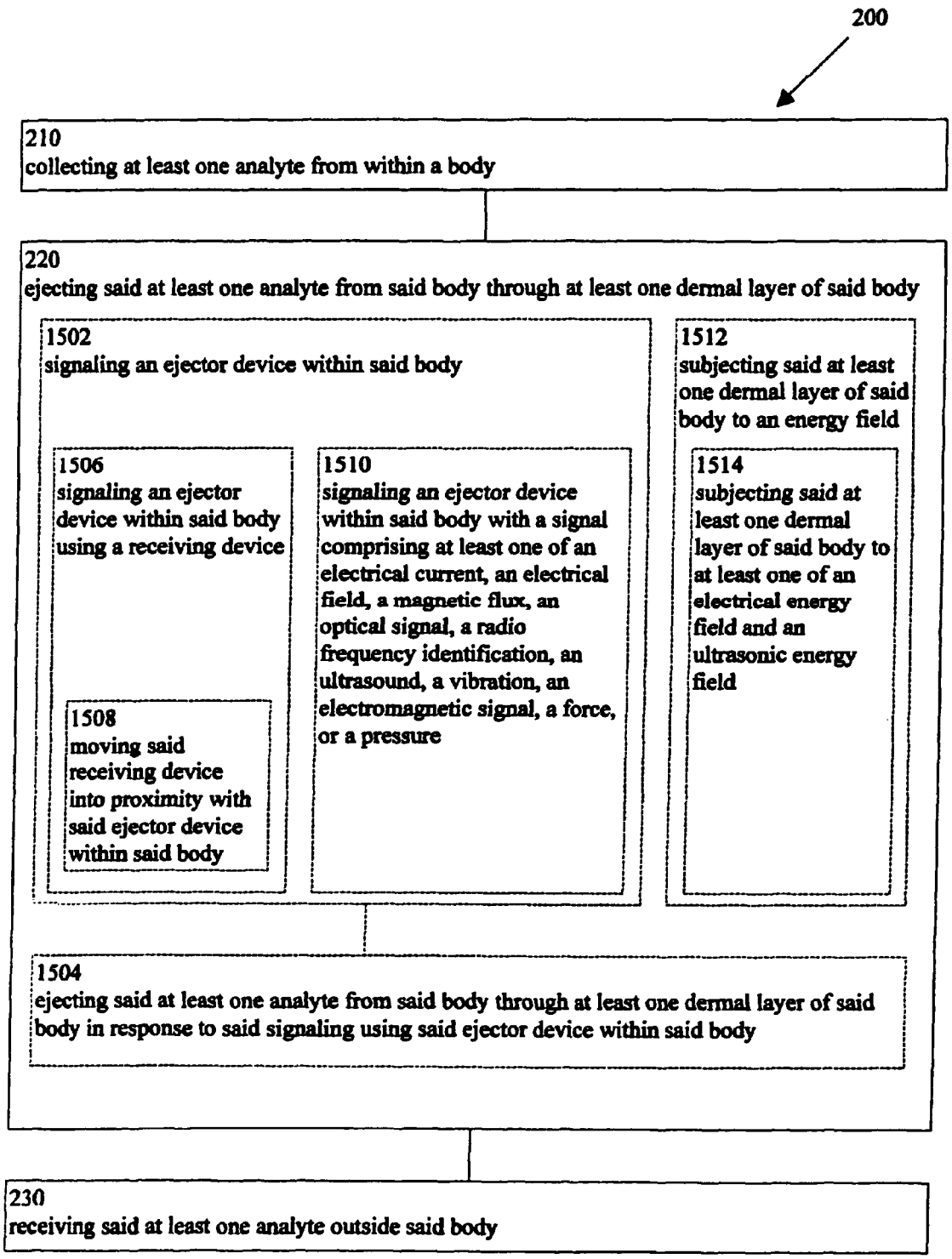
FIG. 15 illustrates an alternative embodiment of the operational flow of FIG. 2.

FIG. 15 illustrates alternative embodiments of the example operational flow 200 of FIG. 2. FIG. 15 illustrates example embodiments where the ejecting operation 220 may include at least one additional operation. Additional operations may include an operation 1502, an operation 1504, an operation 1506, an operation 1508, an operation 1510, an operation 1512, or an operation 1514.

At the operation 1502, an ejector device within said body may be signaled. For example, as shown in FIG. 1b, the ejecting device 103 is signaled by receiving an ejector signal via ejecting device signal receiver 111 sent by receiving device transmitter 113. Then, at the operation 1504, at least one analyte may be ejected from said body through at least one dermal layer of said body using the ejector device within said body in response to the signaling. For example, as shown in FIG. 1b, the ejecting device 103 ejects the collected at least one analyte from the body 101 through at least one dermal layer 102 of the body 101 in response to ejecting device signal receiver 111 receiving an ejection signal. Further, at the operation 1506, an ejector device within said body may be signaled using a receiving device. For example, as shown in FIG. 1b, the ejecting device 103 is signaled by receiving an ejector signal via ejecting device signal receiver 111 sent by the receiving device 104 via receiving device transmitter 113. Further, at the operation 1508, the receiving device may be moved into proximity with the ejector device within said body. For example, as shown in FIG. 1b, the ejecting device signal receiver 111 receives an ejector signal from receiving device transmitter 114 when receiving device 104 is moved into proximity with ejecting device 103. The receiving device 104 may receive a location signal transmitted by the ejecting device 103. Based on the location signal, the receiving device 104 may determine that it is in sufficient proximity to receive the at least one analyte ejected by the ejecting device 103 and receiving device transmitter 113 may then transmit an ejection signal. The receiving device 104 may include one or more processors or memory for determining proximity to the discharging device based on the location signal. Further, at the operation 1510, an ejector device within said body maybe signaled with a signal comprising at least one of an electrical current, an electrical field, a magnetic flux, an optical signal, a radio frequency identification, an ultrasound, a vibration, an electromagnetic signal, a force, or a pressure. For example, as shown in FIG. 1b, the ejecting device 103 is signaled by receiving an ejector signal comprising an electrical current, an electrical field, a magnetic flux, an optical signal, a radio frequency identification, an ultrasound, a vibration, an electromagnetic signal, a force, or a pressure via ejecting device signal receiver 111 sent by receiving device transmitter 113.

At the operation 1512, at least one dermal layer of said body may be subjected to an energy field. For example, as shown in FIG. 1b, the receiving device 104 may subject the at least one dermal layer 102 of the body 101 to an energy field. Subjecting the at least one dermal layer 102 of the body 101 to the energy field may create one or more pores in the at least dermal layer 102 or may increase the permeability of the at least one dermal layer 102, aiding in the ejection of at least one analyte from the body 101 through the at least one dermal layer 102. Further, at the operation 1514, at least one dermal layer of said body may be subjected to at least one of an electrical energy field and an ultrasonic energy field. For example, as shown in FIG. 1b, the receiving device 104 may subject the at least one dermal layer 102 of the body 101 to at least one of an electrical energy field and an ultrasonic energy field.

Figure 16:
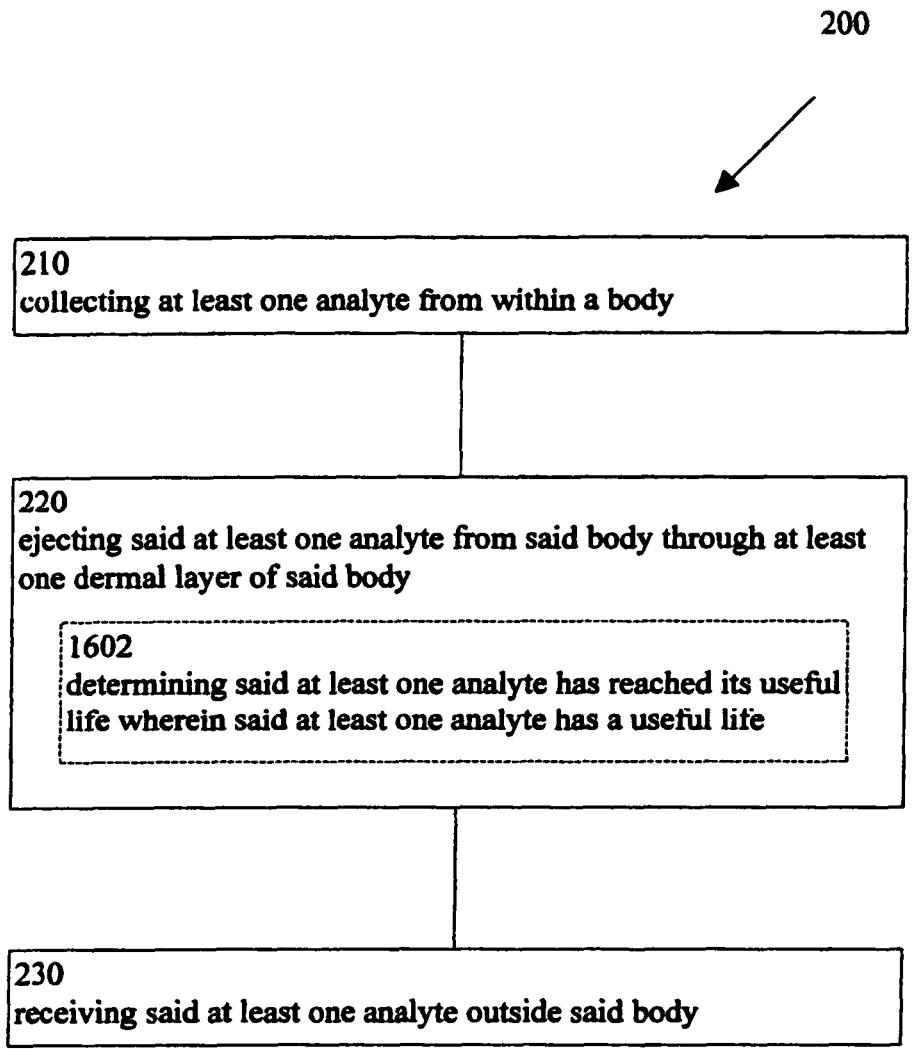
FIG. 16 illustrates an alternative embodiment of the operational flow of FIG. 2.

FIG. 16 illustrates alternative embodiments of the example operational flow 200 of FIG. 2. FIG. 16 illustrates example embodiments where the ejecting operation 220 may include at least one additional operation. Additional operations may include an operation 1602.

At the operation 1602, at least one analyte may be determined to have reached its useful life. For example, as shown in FIG. 1b, the sampling device 120 may be configured to store and dispense a medication that has a useful life, or a period of time after which the medication is not to be dispensed. The sampling device 120 may determine that the useful life for the medication has been exceeded and utilize ejecting device 104 to eject the medication.

Figure 17:
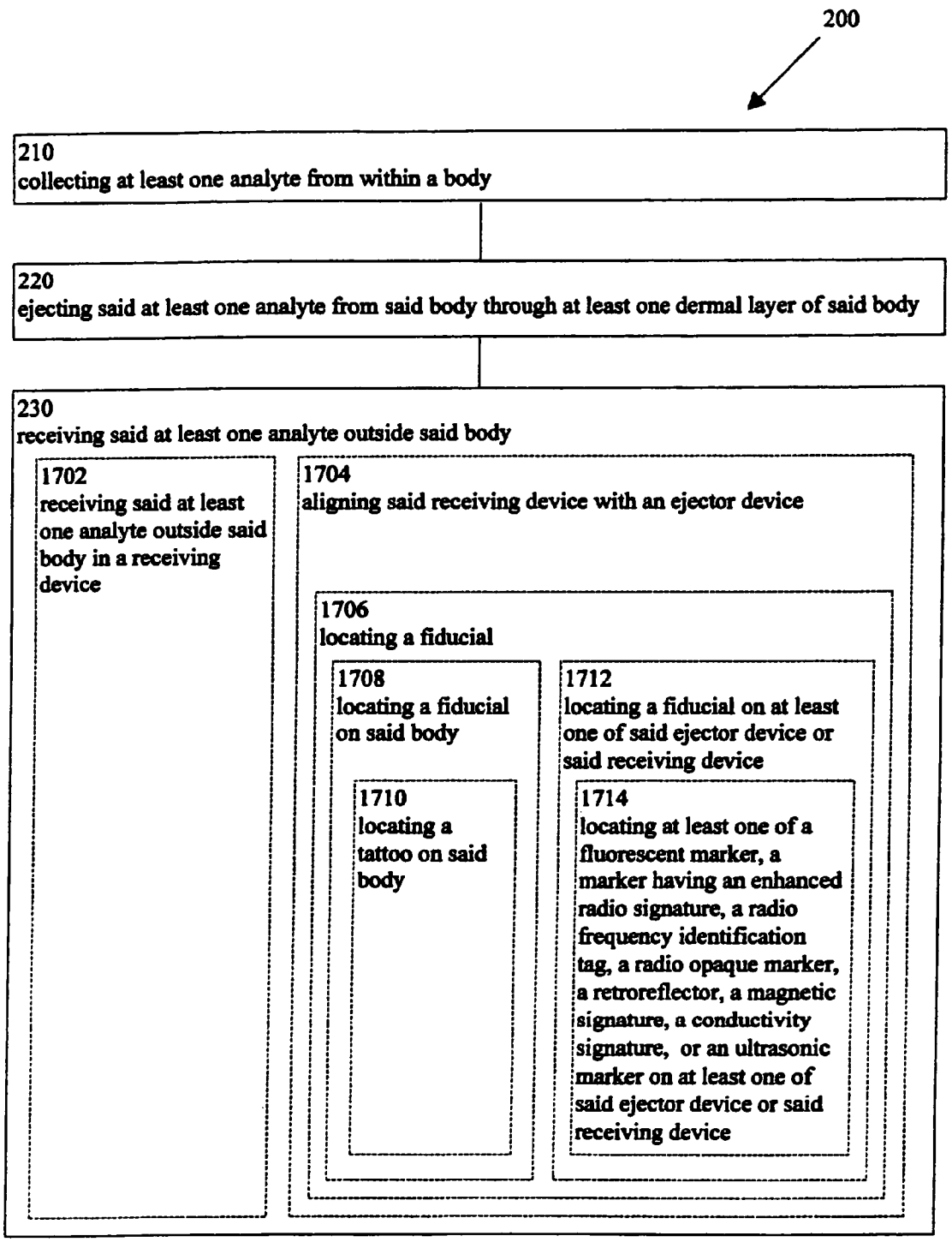
FIG. 17 illustrates an alternative embodiment of the operational flow of FIG. 2.

FIG. 17 illustrates alternative embodiments of the example operational flow 200 of FIG. 2. FIG. 17 illustrates example embodiments where the receiving operation 230 may include at least one additional operation. Additional operations may include an operation 1702, an operation 1704, an operation 1706, an operation 1708, an operation 1710, an operation 1712, or an operation 1714.

At the operation 1702, at least one analyte may be received outside said body in a receiving device. For example, as shown in FIG. 1b, the receiving device 104 receives at least one analyte that has been ejected from the body 101 through at least one dermal layer 102 of the body. The receiving device 104 may include a receptacle for receiving the at least one analyte that has been ejected from the body 101 through at least one dermal layer 102 of the body. Further, at the operation 1704, the receiving device may be aligned with an ejector device. For example, as shown in FIG. 1b, the motorized track system 116 may align receiving device 104 with ejecting device 103 such that a receiving mechanism of receiving device 104 is aligned with the ejector 107 of ejecting device 103. Further, at the operation 1706, a fiducial may be located. For example, as shown in FIG. 1c, the receiving device 104 may be aligned with ejecting device 103 utilizing fiducial 130 as a guide. Further, at the operation 1708, a fiducial may be located on said body. For example, as shown in FIG. 1c, the fiducial 130 may comprise a reference device on the body 101 to guide alignment of receiving device 104 and ejecting device 103. Further, at the operation 1710, a tattoo may be located on said body. For example, as shown in FIG. 1c, the fiducial 130 may comprise a tattoo, or other indicia as desired, on the body for guiding alignment of receiving device 104 and ejecting device 103 such as a dot, bulls eye, cross hairs, and a cross pattern. Alternatively, the tattoo may comprise a cartoon figure where the cartoon character's mouth indicates where the receiving device 104 and ejecting device 103 should be aligned. Further, at the operation 1712, a fiducial may be located on at least one of said ejector device or said receiving device. For example, as shown in FIG. 1b, the ejecting device 103 may include a marker to aid in aligning receiving device 104 and ejecting device 103. Further, at the operation 1714, at least one of a fluorescent marker, a marker having an enhanced radio signature, a radio frequency identification tag, a radio opaque marker, a retroreflector, a magnetic signature, a conductivity signature, or an ultrasonic marker may be located on at least one of said ejector device or said receiving device. For example, as shown in FIG. 1b, the ejecting device may include a fluorescent marker, a marker having an enhanced radio signature, a radio frequency identification tag, a radio opaque marker, a retroreflector, a magnetic signature, a conductivity signature, or an ultrasonic marker to aid in aligning receiving device 104 and ejecting device 103.

Figure 18:
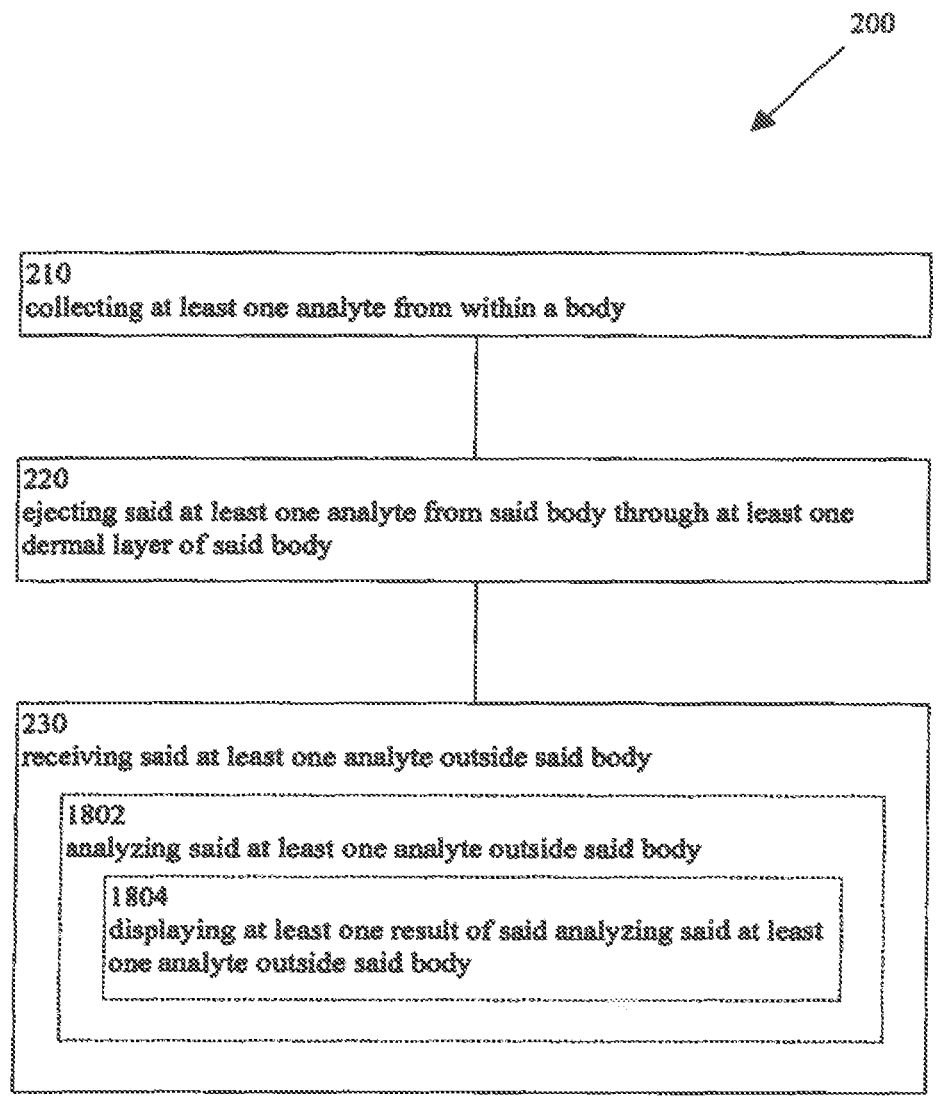
FIG. 18 illustrates an alternative embodiment of the operational flow of FIG. 2.

FIG. 18 illustrates alternative embodiments of the example operational flow 200 of FIG. 2. FIG. 18 illustrates example embodiments where the receiving operation 230 may include at least one additional operation. Additional operations may include an operation 1802, or an operation 1804.

At the operation 1802, at least one analyte may be analyzed outside said body. For example, as shown in FIG. 1a, the receiving device 104 may include a glucose meter for analyzing the glucose level of blood that has been collected, ejected from the body 101 through at least one dermal layer 102 of the body 101, and received. Further, at the operation 1804, at least one result of said analyzing the at least one analyte outside said body may be displayed. For example, as shown in FIG. 1a, the receiving device may detect and display a glucose level of blood that has been collected, ejected from the body 101 through at least one dermal layer 102 of the body 101, and received.

Figure 19:
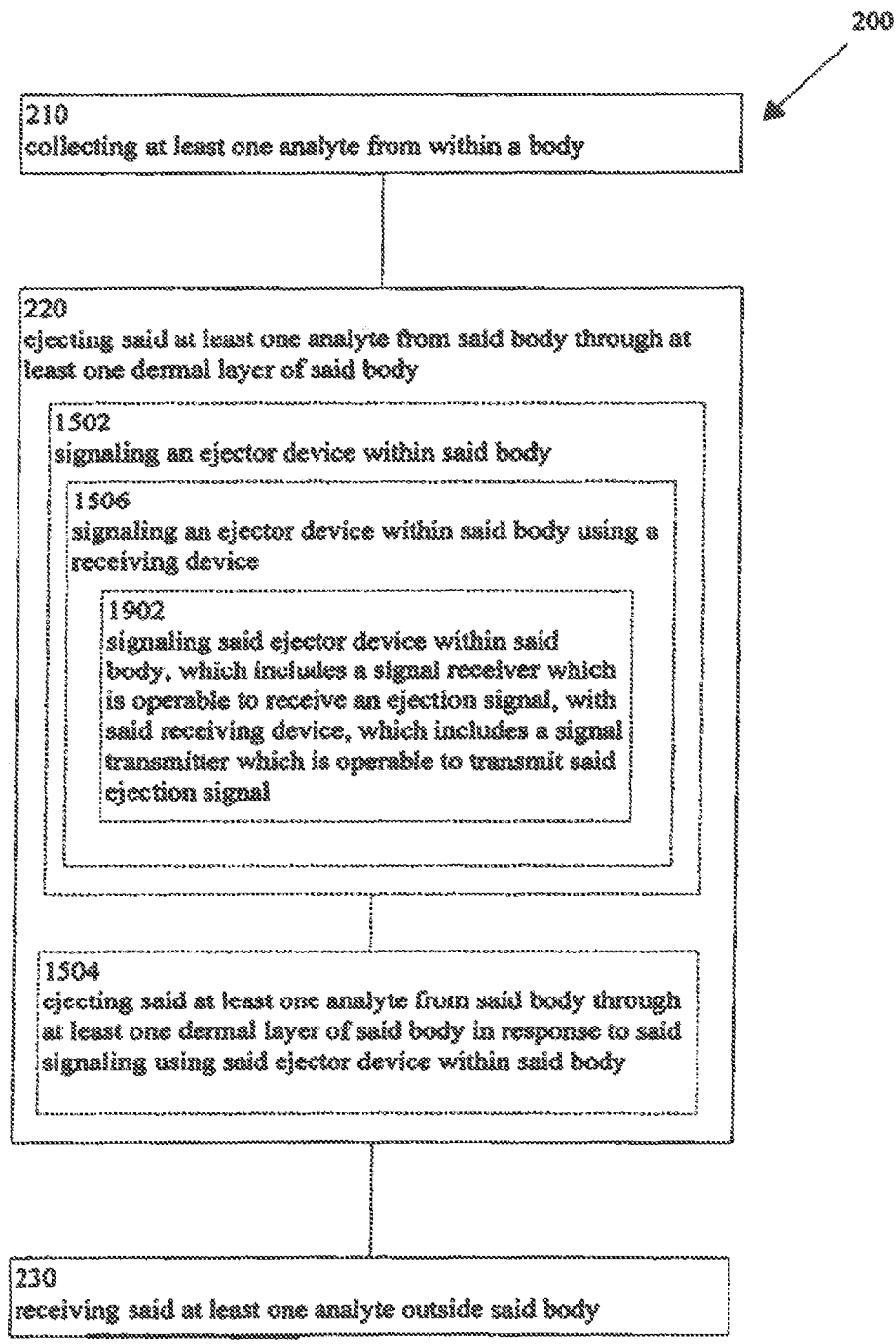
FIG. 19 illustrates an alternative embodiment of the operational flow of FIG. 2.

FIG. 19 illustrates alternative embodiments of the example operational flow 200 of FIG. 2. FIG. 19 illustrates example embodiments where the ejecting operation 220 may include at least one additional operation. Additional operations may include an operation 1902. Further, at the operation 1902, the ejector device within said body, which may include a signal receiver operable to receive an ejection signal, may be signaled an ejection signal transmitted with the receiving device, which may include a signal transmitter operable to transmit said ejection signal. For example, as shown in FIG. 1b, the ejecting device 103 is signaled by receiving an ejector signal via ejecting device signal receiver 111 sent by the receiving device 104 via receiving device transmitter 113.

Figure 20:
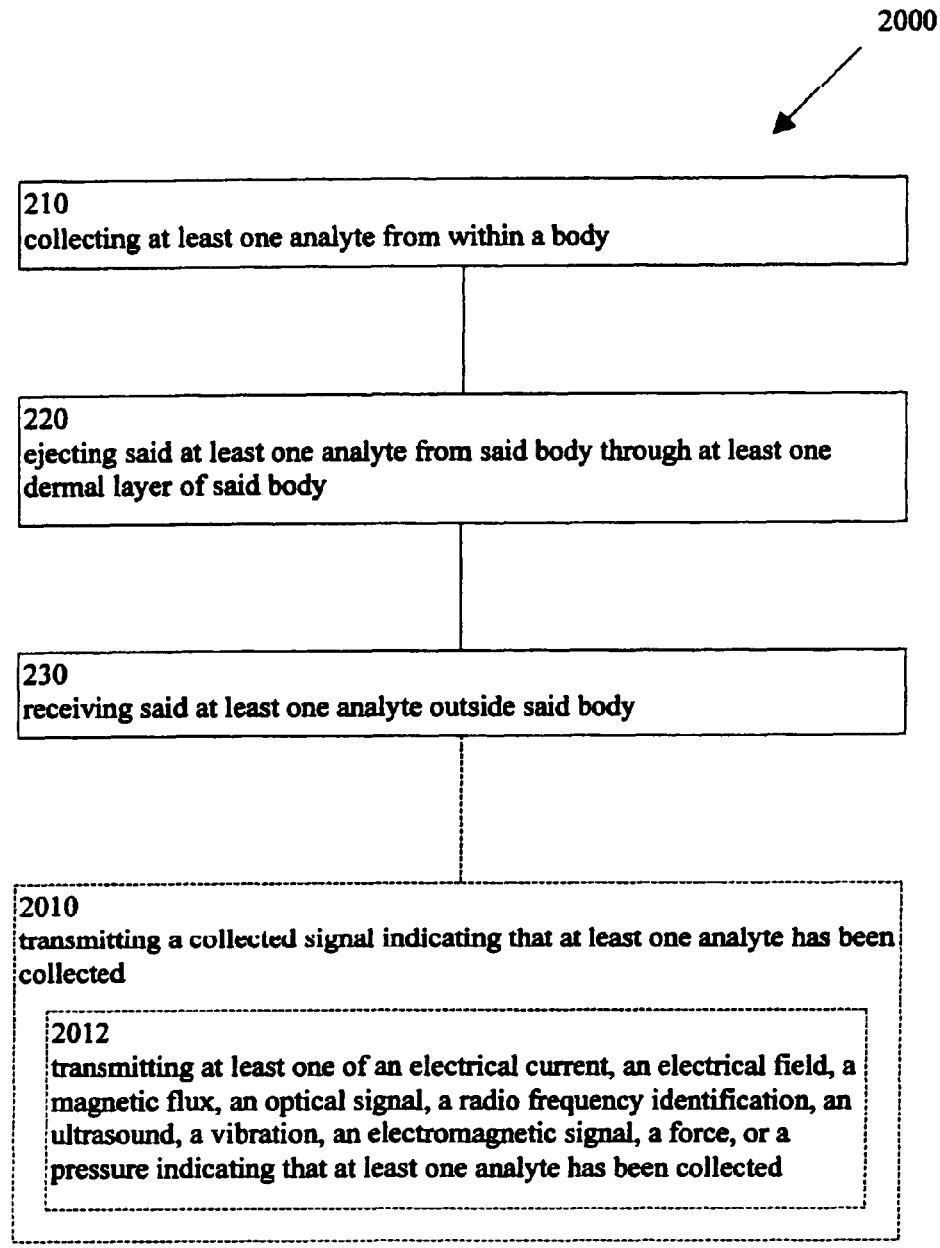
FIG. 20 illustrates an operational flow representing example operations related to obtaining an analyte from a body.

FIG. 20 illustrates an operational flow 2000 representing example operations related to obtaining an analyte from a body. FIG. 20 illustrates an example embodiment where the example operational flow 200 of FIG. 2 may include at least one additional operation. Additional operations may include an operation 2010, or an operation 2012.

After a start operation, a collecting operation 210, an ejecting operation 220, and a receiving operation 230, the operational flow 2000 moves to a transmitting operation 2010, where a collected signal indicating that at least one analyte has been collected may be transmitted. For example, as shown in FIG. 1a, the discharging device 103 includes discharging transmitter 110 which transmits a collected signal when the discharging device 103 has collected at least one analyte.

At the operation 2012, at least one of an electrical current, an electrical field, a magnetic flux, an optical signal, a radio frequency identification, an ultrasound, a vibration, an electromagnetic signal, a force, or a pressure may be transmitted indicating that at least one analyte has been collected. For example, as shown in FIG. 1a, the discharging device 103 includes discharging transmitter 110 which transmits a collected signal when the discharging device 103 has collected at least one analyte where the collected signal is an electrical current, an electrical field, a magnetic flux, an optical signal, a radio frequency identification, an ultrasound, a vibration, an electromagnetic signal, a force, or a pressure.

Figure 21:
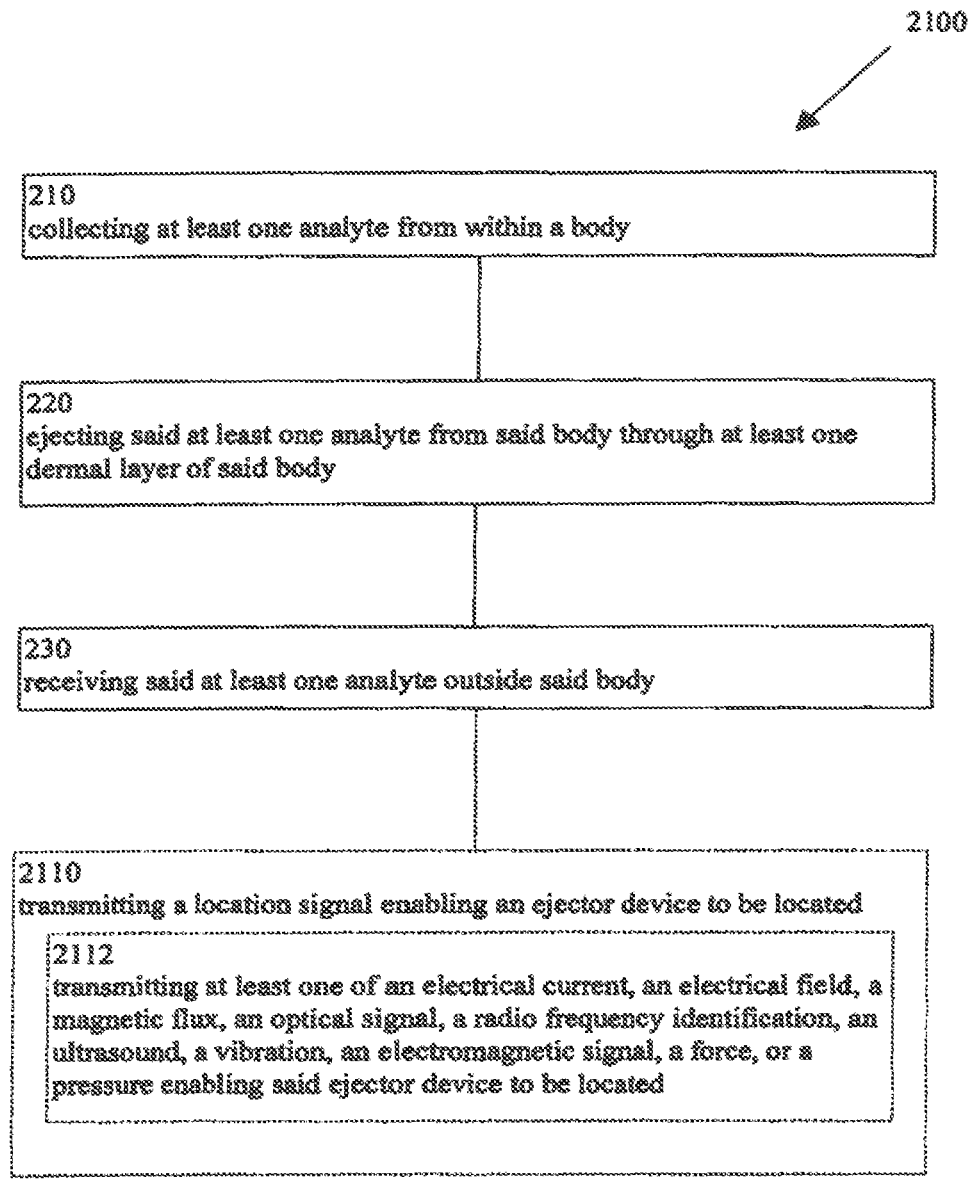
FIG. 21 illustrates an operational flow representing example operations related to obtaining an analyte from a body.

FIG. 21 illustrates an operational flow 2100 representing example operations related to obtaining an analyte from a body. FIG. 21 illustrates an example embodiment where the example operational flow 200 of FIG. 2 may include at least one additional operation. Additional operations may include an operation 2110, or an operation 2112.

After a start operation, a collecting operation 210, an ejecting operation 220, and a receiving operation 230, the operational flow 2100 moves to a transmitting operation 2110, where a location signal enabling an ejector device to be located is transmitted. For example, as shown in FIG. 1b, the ejecting device transmitter 110 of ejecting device 103 transmits a location signal to enable location of the ejecting device 103.

At the operation 2112, at least one of an electrical current, an electrical field, a magnetic flux, an optical signal, a radio frequency identification, an ultrasound, a vibration, an electromagnetic signal, a force, or a pressure enabling said ejector device to be located may be transmitted. For example, as shown in FIG. 1b, the ejecting device transmitter 110 of ejecting device 103 transmits a location signal to enable location of the ejecting device 103 where the location signal is an electrical field, a magnetic flux, an optical signal, a radio frequency identification, an ultrasound, a vibration, an electromagnetic signal, a force, or a pressure.

Figure 22:
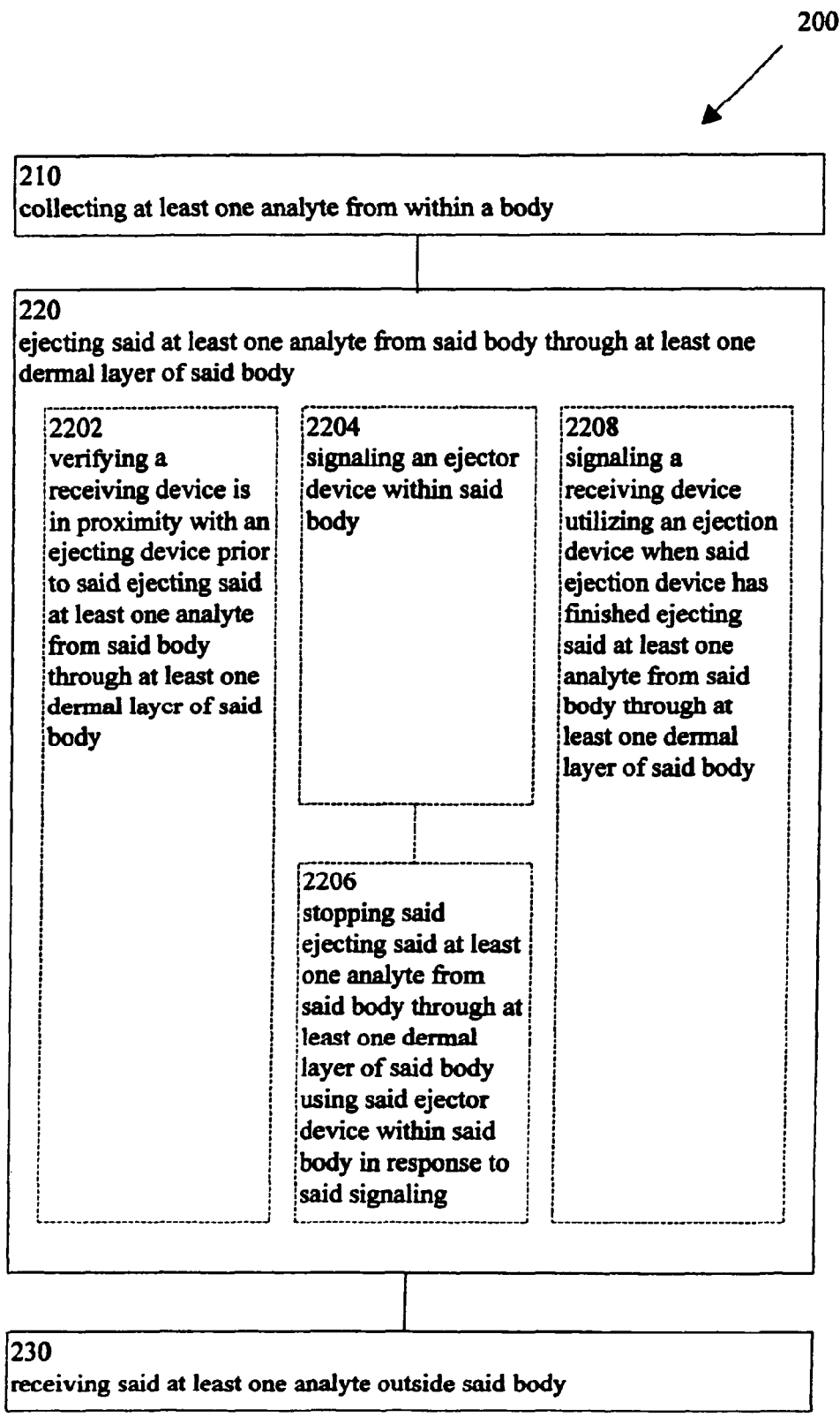
FIG. 22 illustrates an alternative embodiment of the operational flow of FIG. 2.

FIG. 22 illustrates alternative embodiments of the example operational flow 200 of FIG. 2. FIG. 22 illustrates example embodiments where the ejecting operation 220 may include at least one additional operation. Additional operations may include an operation 2202, an operation 2204, an operation 2206, and/or an operation 2208.

At the operation 2202, a receiving device may be verified to be in proximity with an ejecting device prior to ejecting said at least one analyte from said body through at least one dermal layer of said body. For example, as shown in FIG. 1b, the ejecting device 103 may verify that the receiving device 104 is in proximity with the ejecting device 103 prior to ejecting said at least one analyte from said body through at least one dermal layer of said body. The ejecting device 103 may include a locating device for detecting a fiducial included in the receiving device 104. The ejecting device 103 may verify that the receiving device 104 is in proximity with the ejecting device 103 by detecting the fiducial included in the receiving device 104. By way of example, the receiving device 104 may include a RFID tag. The locating device of the ejecting device 103 may detect an RFID tag included in the receiving device 104 by emitting a radio frequency signal and listening for a response emitted by the RFID tag included in the receiving device 104 to verify that the receiving device 104 is in proximity with the ejecting device 103.

At the operation 2204, an ejector device may be signaled within said body. For example, as shown in FIG. 1b, the receiving device 104 may signal ejector device 103 utilizing transmitter 114. Then, at the operation 2206, said ejecting said at least one analyte from said body through at least one dermal layer of said body may be stopped using said ejector device within said body in response to said signaling. For example, as shown in FIG. 1b, the ejector device 103 may be ejecting said at least one analyte from said body through at least one dermal layer of said body. The receiving device 104 may send a stop signal utilizing receiving device transmitter 114 to the ejecting device 103. The receiving device 104 may send a stop signal when the receiving device 104 cannot receive any more of said at least one analyte. The ejecting device 103 may receive the stop signal utilizing ejecting device signal receiver 111. In response to receiving the stop signal, the ejecting device 103 may stop ejecting said at least one analyte from said body through at least one dermal layer of said body.

At the operation 2208, a receiving device may be signaled utilizing an ejection device when said ejection device has finished ejecting said at least one analyte from said body through at least one dermal layer of said body. For example, as shown in FIG. 1b, the ejecting device 103 may send a finished signal to the receiving device 104 utilizing ejecting device transmitter 110 when the ejecting device 103 has finished ejecting said at least one analyte from said body through at least one dermal layer of said body. The receiving device 104 may receive the finished signal utilizing signal receiver 113.

Figure 23:
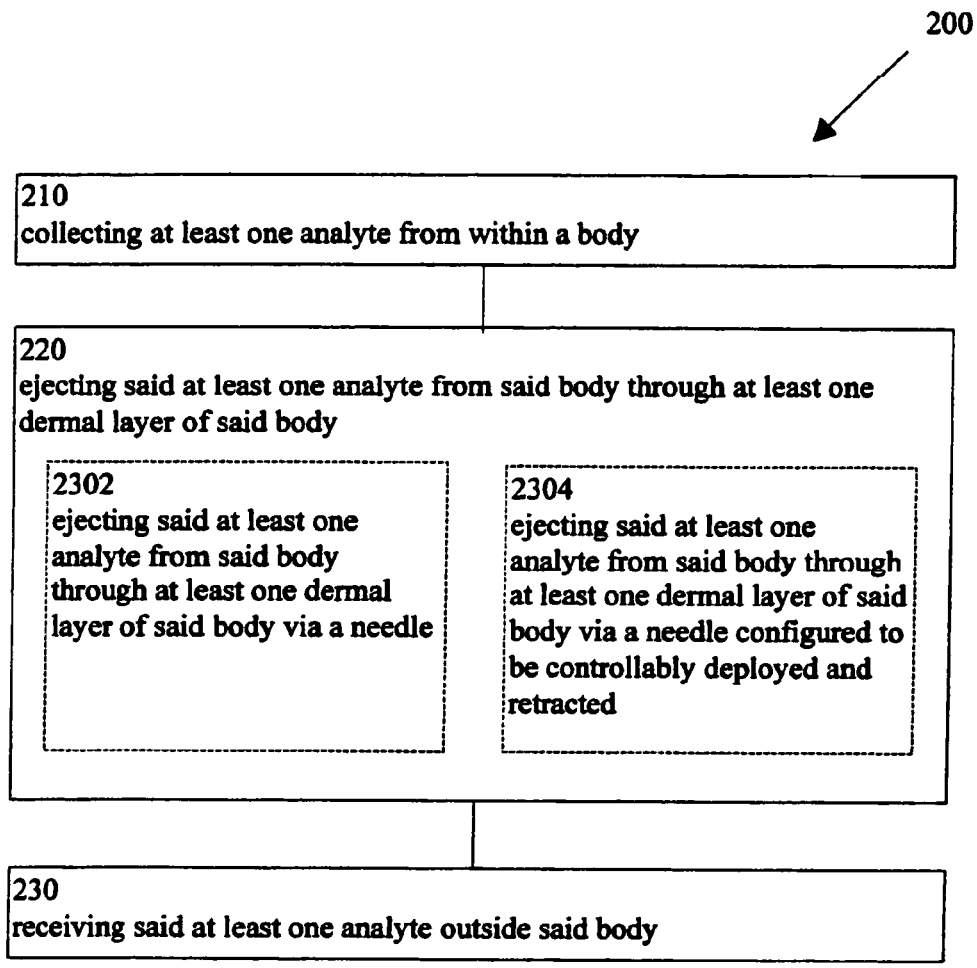
FIG. 23 illustrates an alternative embodiment of the operational flow of FIG. 2.

FIG. 23 illustrates alternative embodiments of the example operational flow 200 of FIG. 2. FIG. 23 illustrates example embodiments where the ejecting operation 220 may include at least one additional operation. Additional operations may include an operation 2302, and/or an operation 2304.

At the operation 2302, at least one analyte may ejected from said body through at least one dermal layer of said body via a needle. For example, as shown in FIG. 1a, ejector 107 may include a needle and may be configured to eject the collected at least one analyte from the body 101 through the at least one dermal layer 102 of the body 101 via the needle.

At the operation 2304, at least one analyte may be ejected from said body through at least one dermal layer of said body via a needle configured to be controllably deployed and retracted. For example, as shown in FIG. 1a, ejector 107 may include a needle. The needle may be configured to be controllably deployed and retracted. The needle may be configured such that the needle does not penetrate through the at least one dermal layer 102 of the body 101 when retracted and does penetrate through the at least one dermal layer 102 of the body 101 when deployed. For example, ejector 107 may be configured to controllably deploy the needle to penetrate through the at least one dermal layer 102 of the body 101, eject the collected at least one analyte from the body 101 through the at least one dermal layer 102 of the body 101 via the needle, and then retract the needle.

Figure 24:
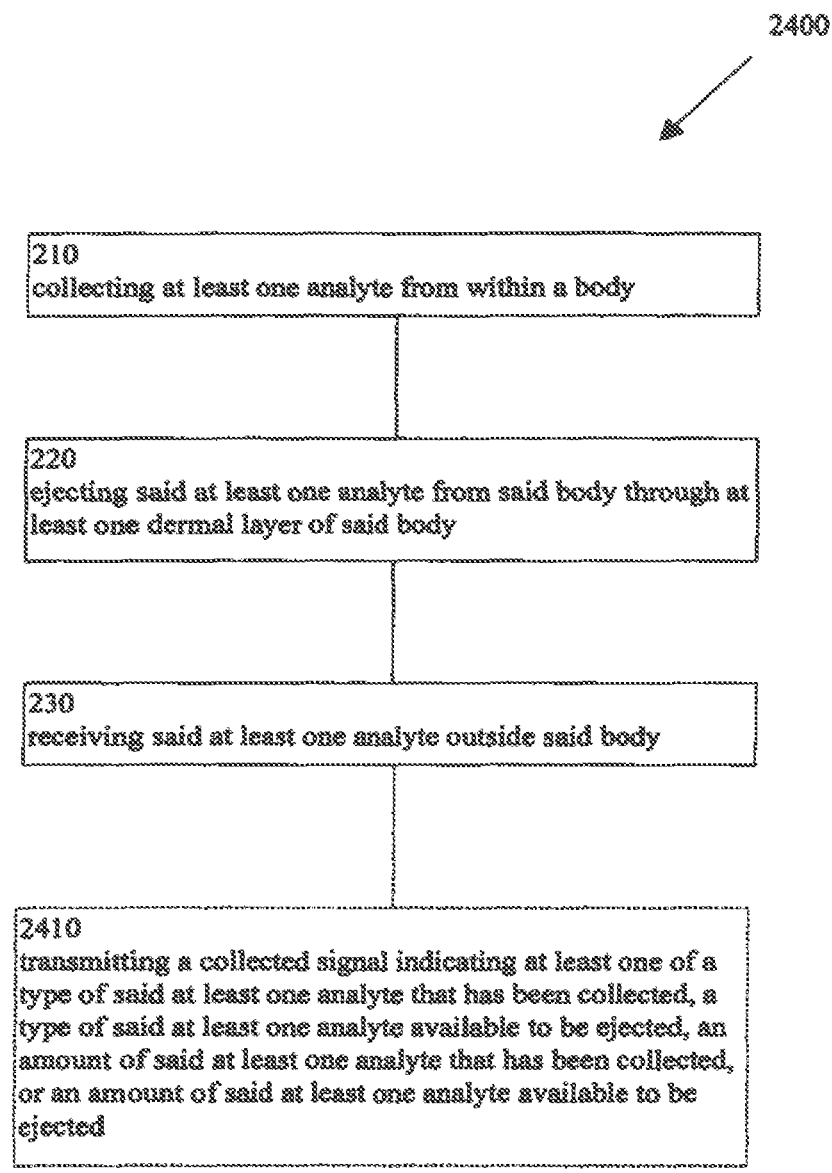
FIG. 24 illustrates an operational flow representing example operations related to obtaining an analyte from a body.

FIG. 24 illustrates an operational flow 2400 representing example operations related to obtaining an analyte from a body. FIG. 24 illustrates an example embodiment where the example operational flow 200 of FIG. 2 may include at least one additional operation. Additional operations may include an operation 2410.

After a start operation, a collecting operation 210, an ejecting operation 220, and a receiving operation 230, the operational flow 2400 moves to a transmitting operation 2410, where a collected signal is transmitted indicating at least one of a type of said at least one analyte that has been collected, a type of said at least one analyte available to be ejected, an amount of said at least one analyte that has been collected, or an amount of said at least one analyte available to be ejected. For example, as shown in FIG. 1a, the discharging transmitter 110 may transmit a collected signal when the discharging device 103 has collected at least one analyte. The collected signal may include that proteins are available to be ejected or that 10 µL of cerebral spinal fluid has been collected.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes or systems or other technologies described herein can be effected (e.g., hardware, software, or firmware), and that the preferred vehicle will vary with the context in which the processes or systems or other technologies are deployed. For example, if an implementer determines that speed and accuracy are paramount, the implementer may opt for a mainly hardware or firmware vehicle; alternatively, if flexibility is paramount, the implementer may opt for a mainly software implementation; or, yet again alternatively, the implementer may opt for some combination of hardware, software, or firmware. Hence, there are several possible vehicles by which the processes or devices or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices or processes via the use of block diagrams, flowcharts, or examples. Insofar as such block diagrams, flowcharts, or examples contain one or more functions or operations, it will be understood by those within the art that each function or operation within such block diagrams, flowcharts, or examples can be implemented, individually or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes or devices described herein, or a microprocessor configured by a computer program which at least partially carries out processes or devices described herein), electrical circuitry forming a memory device (e.g., forms of random access, flash, read only, etc.)), or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), or control systems including feedback loops and control motors (e.g., feedback for sensing position or velocity; control motors for moving or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components or inactive-state components or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). It will be further understood by those within the art that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A system, comprising:
    means for collecting at least one analyte from within a body;
    means for ejecting said at least one analyte from said body through at least one dermal layer of said body;
    means for receiving said at least one analyte outside said body, said receiving means including a means for charging an energy storage mechanism of said collecting means via an energy source located outside said body, located inside said body, or located both outside said body and inside said body.

2. The system of claim 1, further comprising:
    means for transferring said at least one analyte from said collecting means within said body to said ejecting means within said body.

3. The system of claim 2, wherein said collecting means is located distal to said ejecting means and said at least one analyte is transported to said ejecting means.

4. A system, comprising:
    means for collecting at least one analyte from within a body;
    means for ejecting said at least one analyte from said body through at least one dermal layer of said body;
    means for receiving said at least one analyte outside said body; and
    means for powering said collecting means via an energy source located outside said body, located inside said body, or located both outside said body and inside said body.

5. The system of claim 4, wherein said means for powering said collecting means via an energy source located outside said body, located inside said body, or located both outside said body and inside said body comprises:
    means for powering said collecting means via said means for receiving said at least one analyte outside said body.

6. The system of claim 4, further comprising:
    means for transmitting a location signal enabling said ejecting means to be located.

7. The system of claim 6, wherein said location signal comprises at least one of an electrical current, an electrical field, a magnetic flux, an optical signal, a radio frequency identification, an ultrasound, a vibration, an electromagnetic force, a force, or a pressure.

8. The system of claim 4, further comprising:
    means for sorting said at least one analyte.

9. The system of claim 4, further comprising:
    means for concentrating said at least one analyte.

10. The system of claim 4, further comprising:
    means for diluting said at least one analyte.

11. The system of claim 4, wherein said means for collecting at least one analyte from within a body comprises:
   means for collecting at least a portion of at least one of cells, proteins, bacteria, blood, a blood component, molecules, viruses, viral particles, pathogens, parasites, malarial parasites, oglionucleotides, lymph, a lymph component, or cerebral spinal fluid.

12. The system of claim 11, wherein said blood component comprises at least one of plasma or serum.

13. The system of claim 4, wherein said means for receiving said at least one analyte outside said body comprises:
   means for receiving said at least one analyte outside said body in a receiving device.

14. The system of claim 4, further comprising:
   means for transferring said at least one analyte from said collecting means within said body to said ejecting means within said body.

15. A system, comprising:
   means for collecting at least one analyte from within a body;
   means for ejecting said at least one analyte from said body through at least one dermal layer of said body; and
   means for receiving said at least one analyte outside said body, said receiving means including a means for charging an energy storage mechanism of said ejecting means via an energy source located outside said body, located inside said body, or located both outside said body and inside said body.

16. The system of claim 15, further comprising:
   means for transferring said at least one analyte from said collecting means within said body to said ejecting means within said body.

17. A system, comprising:
   means for collecting at least one analyte from within a body;
   means for ejecting said at least one analyte from said body through at least one dermal layer of said body; and
   means for receiving said at least one analyte outside said body, said receiving means including a means for powering said ejecting means via an energy source located outside said body, located inside said body, or located both outside said body and inside said body.

18. The system of claim 17, further comprising:
   means for transferring said at least one analyte from said collecting means within said body to said ejecting means within said body.

19. A system, comprising:
   means for collecting at least one analyte from within a body;
   means for ejecting said at least one analyte from said body through at least one dermal layer of said body via a microjet; and
   means for receiving said at least one analyte outside said body.

20. The system of claim 19, wherein said means for ejecting said at least one analyte from said body through at least one dermal layer of said body via a microjet comprises:
   means for ejecting said at least one analyte from said body through at least one dermal layer of said body via a liquid microjet.

21. The system of claim 20, wherein said means for ejecting said at least one analyte from said body through at least one dermal layer of said body via a liquid microjet comprises:
   means for ejecting said at least one analyte from said body through at least one dermal layer of said body via a pulsed liquid microjet.

22. The system of claim 19, further comprising:
   means for transferring said at least one analyte from said collecting means within said body to said ejecting means within said body.

23. A system, comprising:
   means for collecting at least one analyte from within a body;
   means for ejecting said at least one analyte from said body through at least one dermal layer of said body, the ejecting means including a means for generating pressure utilizing a piezoelectric pressure generating mechanism; and
   means for receiving said at least one analyte outside said body.

24. The system of claim 23, further comprising:
   means for transferring said at least one analyte from said collecting means within said body to said ejecting means within said body.

25. A system, comprising:
   means for collecting at least one analyte from within a body;
   means for ejecting said at least one analyte from said body through at least one dermal layer of said body via a needle originating from a subdermal location within said body; and
   means for receiving said at least one analyte outside said body.

26. A system, comprising:
   means for collecting at least one analyte from within a body;
   means for ejecting said at least one analyte from said body through at least one dermal layer of said body via a needle configured to be controllably deployed and retracted, wherein said needle is located subdermally when retracted, and wherein at least a portion of said needle penetrates through said at least one dermal layer when deployed; and
   means for receiving said at least one analyte outside said body.

* * * * *